US012170143B1

(12) United States Patent
Sanidas et al.

(10) Patent No.: US 12,170,143 B1
(45) Date of Patent: Dec. 17, 2024

(54) MULTI-SIDED MATCH MAKING PLATFORMS

(71) Applicant: State Farm Mutual Automobile Insurance Company, Bloomington, IL (US)

(72) Inventors: Tim G. Sanidas, Bloomington, IL (US); Edward P. Matesevac, Normal, IL (US); Anthony Nathan Noel, Bloomington, IL (US); Chris Kawakita, Normal, IL (US); Garrick Douglas Gabbrants, Bloomington, IL (US)

(73) Assignee: State Farm Mutual Automobile Insurance Company, Bloomington, IL (US)

( * ) Notice: Subject to any disclaimer, the term of this patent is extended or adjusted under 35 U.S.C. 154(b) by 0 days.

(21) Appl. No.: 16/918,876

(22) Filed: Jul. 1, 2020

Related U.S. Application Data

(60) Provisional application No. 62/870,528, filed on Jul. 3, 2019.

(51) Int. Cl.
*G16H 40/20* (2018.01)
*G06N 20/00* (2019.01)
*G16H 40/67* (2018.01)

(52) U.S. Cl.
CPC ............. *G16H 40/20* (2018.01); *G06N 20/00* (2019.01); *G16H 40/67* (2018.01)

(58) Field of Classification Search
CPC ........ G06Q 50/22; G06Q 50/23; G06Q 50/24; G06Q 50/20–26; G16H 40/20; G16H 40/67; G06N 20/00
(Continued)

(56) References Cited

U.S. PATENT DOCUMENTS 1,446,000 A 2/1923 Cleland
5,553,609 A 9/1996 Chen et al.
(Continued)

FOREIGN PATENT DOCUMENTS

CA 2781251 A1 12/2013
IN 201811043670 A 7/2018
(Continued)

OTHER PUBLICATIONS

Marcelino I, Lopes D, Reis M, Silva F, Laza R, Pereira A. Using the eServices platform for detecting behavior patterns deviation in the elderly assisted living: a case study. Biomed Res Int. 2015;2015:530828. doi: 10.1155/2015/530828. Epub Mar. 22, 2015. PMID: 25874219; PMCID: PMC4385593. (Year: 2015).*
(Continued)

*Primary Examiner* — Christopher L Gilligan
*Assistant Examiner* — Jessica Marie Webb
(74) *Attorney, Agent, or Firm* — Armstrong Teasdale LLP

(57) ABSTRACT

A multi-sided match making ("MMM") computer system including at least one processor in communication with at least one memory device for matching consumers to providers is provided. The at least one processor is configured to: (i) receive registration data from a user, (ii) receive user data from at least one of a sensor and a mobile device associated with the user, (iii) analyze the registration data and the user data, (iv) determine a need based upon the analyzed registration and user data, (v) transmit the determined need to at least one caregiver associated with the user, and (vi) match the user to at least one provider based upon the determined need, wherein the provider is at least one of the caregiver, another caregiver, and a service, and wherein the provider is able to meet the determined need for the user.

19 Claims, 7 Drawing Sheets

(58) Field of Classification Search
USPC .................................................. 705/2, 3, 4
See application file for complete search history.

(56) References Cited

U.S. PATENT DOCUMENTS 5,935,251 A 8/1999 Moore
5,967,975 A 10/1999 Ridgeway
6,428,475 B1 8/2002 Shen
6,611,206 B2 8/2003 Eshelman et al.
6,847,892 B2 1/2005 Zhou et al.
6,886,139 B2 4/2005 Liu
7,091,865 B2 8/2006 Cuddihy et al.
7,154,399 B2 12/2006 Cuddihy et al.
7,242,305 B2 7/2007 Cuddihy et al.
7,301,463 B1 11/2007 Paterno
7,397,346 B2 7/2008 Helal et al.
7,411,510 B1 8/2008 Nixon
7,498,985 B1 3/2009 Woo et al.
7,502,498 B2 3/2009 Wen et al.
7,562,121 B2 7/2009 Berisford et al.
7,586,418 B2 9/2009 Cuddihy et al.
7,733,224 B2 6/2010 Tran
7,801,612 B2 9/2010 Johnson
7,831,235 B2 11/2010 Mononen
7,835,926 B1 11/2010 Naidoo
7,865,386 B2 1/2011 Sarkar
7,911,334 B2 3/2011 Busey
7,966,378 B2 6/2011 Berisford et al.
8,019,622 B2 9/2011 Kaboff et al.
8,050,665 B1 11/2011 Orbach
8,214,082 B2 7/2012 Tsai et al.
8,346,594 B2 1/2013 Begeja et al.
8,490,006 B1 7/2013 Reeser et al.
8,527,306 B1 9/2013 Reeser et al.
8,529,456 B2 9/2013 Cobain
8,533,144 B1 9/2013 Reeser et al.
8,640,038 B1 1/2014 Reeser et al.
8,665,084 B2 3/2014 Shapiro et al.
8,669,864 B1 3/2014 Tedesco et al.
8,670,998 B2 3/2014 Bertha et al.
8,675,920 B2 3/2014 Hanson et al.
8,676,833 B2 3/2014 Chunilal
8,682,952 B2 3/2014 Kutzik et al.
8,744,901 B2 6/2014 Begeja et al.
8,803,690 B2 8/2014 Junqua et al.
8,856,383 B2 10/2014 Beninato et al.
8,868,616 B1 10/2014 Otto et al.
8,882,666 B1 11/2014 Goldberg et al.
8,890,680 B2 11/2014 Reeser et al.
8,917,186 B1 12/2014 Grant
8,929,853 B2 1/2015 Butler
8,965,327 B2 2/2015 Davis et al.
8,976,937 B2 3/2015 Shapiro et al.
9,049,168 B2 6/2015 Jacob et al.
9,057,746 B1 6/2015 Houlette et al.
9,117,349 B2 8/2015 Shapiro et al.
9,142,119 B1 9/2015 Grant
9,152,737 B1 10/2015 Micali et al.
9,165,334 B2 10/2015 Simon
9,183,578 B1 11/2015 Reeser et al.
9,202,363 B1 12/2015 Grant
9,208,661 B2 12/2015 Junqua et al.
9,262,909 B1 2/2016 Grant
9,286,772 B2 3/2016 Shapiro et al.
9,344,330 B2 5/2016 Jacob et al.
9,349,300 B2 5/2016 Harkness
9,375,142 B2 6/2016 Schultz
9,408,561 B2 8/2016 Stone et al.
9,424,737 B2 8/2016 Bailey et al.
9,443,195 B2 9/2016 Micali et al.
9,472,092 B1 10/2016 Grant
9,491,277 B2 * 11/2016 Vincent .................. H04W 4/90
9,536,052 B2 1/2017 Amarasingham et al.
9,585,563 B2 3/2017 Mensinger et al.
9,589,441 B2 3/2017 Shapiro et al.
9,609,003 B1 3/2017 Chmielewski et al.
9,665,892 B1 5/2017 Reeser et al.
9,666,060 B2 5/2017 Reeser et al.
9,699,529 B1 7/2017 Petri et al.
9,712,576 B1 * 7/2017 Gill ................. G06Q 10/06311
9,739,813 B2 8/2017 Houlette et al.
9,754,477 B2 9/2017 Poder
9,767,680 B1 9/2017 Trundle
9,786,158 B2 10/2017 Beaver et al.
9,798,979 B2 10/2017 Fadell et al.
9,798,993 B2 10/2017 Payne et al.
9,800,570 B1 10/2017 Bleisch
9,800,958 B1 10/2017 Petri et al.
9,801,541 B2 10/2017 Mensinger
9,812,001 B1 11/2017 Grant
9,838,854 B2 12/2017 Fretwell
9,866,507 B2 1/2018 Frenkel et al.
9,888,371 B1 2/2018 Jacob
9,892,463 B1 2/2018 Hakimi-Boushehri et al.
9,898,168 B2 2/2018 Shapiro et al.
9,898,912 B1 2/2018 Jordan, II et al.
9,901,252 B2 * 2/2018 Tran ..................... A61B 5/1117
9,911,042 B1 3/2018 Cardona et al.
9,922,524 B2 3/2018 Devdas et al.
9,923,971 B2 3/2018 Madey et al.
9,942,630 B1 4/2018 Petri et al.
9,947,202 B1 4/2018 Moon et al.
9,978,033 B1 5/2018 Payne et al.
9,997,056 B2 6/2018 Bleisch
10,002,295 B1 6/2018 Cardona et al.
10,022,084 B2 7/2018 Nonaka et al.
10,042,341 B1 8/2018 Jacob
10,043,369 B2 8/2018 Hopkins et al.
10,047,974 B1 8/2018 Riblet et al.
10,055,793 B1 8/2018 Call et al.
10,055,803 B2 8/2018 Orduna et al.
10,057,664 B1 8/2018 Moon et al.
10,073,929 B2 9/2018 Vaynriber et al.
10,102,584 B1 10/2018 Devereaux et al.
10,102,585 B1 10/2018 Bryant et al.
10,107,708 B1 10/2018 Schick et al.
10,136,294 B2 11/2018 Mehta et al.
10,140,666 B1 11/2018 Wang et al.
10,142,394 B2 11/2018 Chmielewski et al.
10,147,296 B2 12/2018 Gregg
10,152,150 B2 12/2018 Sherman
10,176,705 B1 1/2019 Grant
10,181,160 B1 1/2019 Hakimi-Boushehri et al.
10,181,246 B1 1/2019 Jackson
10,186,134 B1 1/2019 Moon et al.
10,198,771 B1 2/2019 Madigan et al.
10,204,500 B2 2/2019 Cullin et al.
10,206,630 B2 2/2019 Stone et al.
10,217,068 B1 2/2019 Davis et al.
10,226,187 B2 3/2019 Al-Ali et al.
10,226,204 B2 3/2019 Heaton et al.
10,229,394 B1 3/2019 Davis et al.
10,244,294 B1 3/2019 Moon et al.
10,249,158 B1 4/2019 Jordan, II et al.
10,258,295 B2 4/2019 Fountaine
10,282,787 B1 5/2019 Hakimi-Boushehri et al.
10,282,788 B1 5/2019 Jordan, II et al.
10,282,961 B1 5/2019 Jordan, II et al.
10,295,431 B1 5/2019 Schick et al.
10,297,138 B2 5/2019 Reeser et al.
10,298,735 B2 5/2019 Preston et al.
10,304,311 B2 5/2019 Clark et al.
10,304,313 B1 5/2019 Moon et al.
10,319,209 B2 6/2019 Carlton-Foss
10,323,860 B1 6/2019 Riblet et al.
10,325,471 B1 6/2019 Victor
10,325,473 B1 6/2019 Moon et al.
10,332,059 B2 6/2019 Matsuoka et al.
10,335,059 B2 7/2019 Annegam et al.
10,346,811 B1 7/2019 Jordan, II et al.
10,353,359 B1 7/2019 Jordan, II et al.
10,356,303 B1 7/2019 Jordan, II et al.
10,360,345 B2 7/2019 Ramsdell
10,373,257 B1 8/2019 Iqbal et al.

(56) References Cited

U.S. PATENT DOCUMENTS 10,380,692 B1 8/2019 Parker et al.
10,387,966 B1 8/2019 Shah et al.
10,388,135 B1 8/2019 Jordan, II et al.
10,412,169 B1 9/2019 Madey et al.
10,446,000 B2 10/2019 Friar et al.
10,446,007 B2 10/2019 Kawazu et al.
10,467,476 B1 11/2019 Cardona et al.
10,475,141 B2 11/2019 McIntosh et al.
10,480,825 B1 11/2019 Riblet et al.
10,482,746 B1 11/2019 Moon et al.
10,506,411 B1 12/2019 Jacob
10,506,990 B2 12/2019 Lee et al.
10,514,669 B1 12/2019 Call et al.
10,515,372 B1 12/2019 Jordan, II et al.
10,522,009 B1 12/2019 Jordan, II et al.
10,522,021 B1 12/2019 Victor
10,546,478 B1 1/2020 Moon et al.
10,547,918 B1 1/2020 Moon et al.
10,548,512 B2 2/2020 Hausdorff et al.
10,565,541 B2 2/2020 Payne et al.
10,573,146 B1 2/2020 Jordan, II et al.
10,573,149 B1 2/2020 Jordan, II et al.
10,579,028 B1 3/2020 Jacob
10,586,177 B1 3/2020 Choueiter et al.
10,607,295 B1 3/2020 Hakimi-Boushehri et al.
10,621,686 B2 4/2020 Mazar et al.
10,623,790 B2 4/2020 Maddalena
10,634,576 B1 4/2020 Schick et al.
10,679,292 B1 6/2020 Call et al.
10,685,402 B1 6/2020 Bryant et al.
10,726,494 B1 7/2020 Shah et al.
10,726,500 B1 7/2020 Shah et al.
10,733,671 B1 8/2020 Hakimi-Boushehri et al.
10,733,868 B2 8/2020 Moon et al.
10,735,829 B2 8/2020 Petri et al.
10,740,691 B2 8/2020 Choueiter et al.
10,741,033 B1 8/2020 Jordan, II et al.
10,750,252 B2 8/2020 Petri et al.
10,795,329 B1 10/2020 Jordan, II et al.
10,796,557 B2 10/2020 Sundermeyer et al.
10,823,458 B1 11/2020 Riblet et al.
10,824,971 B1 11/2020 Davis et al.
10,825,318 B1 11/2020 Williams et al.
10,825,320 B1 11/2020 Moon et al.
10,825,321 B2 11/2020 Moon et al.
10,832,225 B1 11/2020 Davis et al.
10,846,800 B1 11/2020 Bryant et al.
10,878,062 B1 * 12/2020 Garavaglia ............ G16H 40/60
10,922,756 B1 2/2021 Call et al.
10,922,948 B1 2/2021 Moon et al.
10,943,447 B1 3/2021 Jordan, II et al.
10,970,990 B1 4/2021 Jacob
10,990,069 B1 4/2021 Jacob
11,004,320 B1 5/2021 Jordan, II et al.
11,015,997 B1 5/2021 Schick et al.
11,017,480 B2 5/2021 Shah et al.
11,024,142 B2 6/2021 Tunnell
11,042,137 B1 6/2021 Call et al.
11,042,942 B1 6/2021 Hakimi-Boushehri et al.
11,043,098 B1 6/2021 Jordan, II et al.
11,049,078 B1 6/2021 Jordan, II et al.
11,049,189 B2 6/2021 Shah et al.
11,074,659 B1 7/2021 Hakimi-Boushehri et al.
11,094,180 B1 8/2021 Williams et al.
11,107,465 B2 8/2021 Gustman et al.
11,118,812 B1 9/2021 Riblet et al.
11,120,226 B1 * 9/2021 Nudd ..................... G16H 50/30
11,126,708 B2 9/2021 Reimer
11,188,840 B1 11/2021 Rivera et al.
11,431,660 B1 8/2022 Leeds et al.
11,581,099 B1 * 2/2023 Rufo ..................... G16H 20/13
11,587,555 B1 2/2023 Pathak
2002/0046047 A1 4/2002 Budd
2002/0116256 A1 8/2002 de Rafael et al.
2002/0194048 A1 12/2002 Levinson
2003/0001742 A1 1/2003 Eshelman et al.
2003/0023459 A1 1/2003 Shipon
2003/0144793 A1 7/2003 Melaku et al.
2004/0030531 A1 2/2004 Miller
2004/0078220 A1 4/2004 Jackson
2004/0220538 A1 11/2004 Panopoulos
2004/0249250 A1 12/2004 McGee et al.
2005/0137465 A1 6/2005 Cuddihy et al.
2005/0142524 A1 6/2005 Simon et al.
2005/0174242 A1 8/2005 Cohen
2005/0228245 A1 10/2005 Quy
2006/0143060 A1 6/2006 Conry et al.
2006/0205564 A1 9/2006 Peterson
2007/0186165 A1 8/2007 Maislos et al.
2007/0214002 A1 9/2007 Smith
2007/0250791 A1 10/2007 Halliday et al.
2007/0274464 A1 11/2007 Cameron
2007/0282476 A1 12/2007 Song et al.
2008/0084296 A1 4/2008 Kutzik
2008/0154099 A1 6/2008 Aspel et al.
2008/0201174 A1 8/2008 Ramasubramanian et al.
2008/0235629 A1 9/2008 Porter et al.
2008/0240379 A1 10/2008 Maislos et al.
2008/0292151 A1 11/2008 Kurtz et al.
2008/0294462 A1 * 11/2008 Nuhaan .............. G06Q 10/1095 705/2
2008/0294490 A1 11/2008 Nuhaan
2009/0010106 A1 1/2009 Levy
2009/0012373 A1 1/2009 Raij et al.
2009/0048865 A1 2/2009 Breazeale, Jr.
2009/0259492 A1 10/2009 Cossman
2009/0265185 A1 10/2009 Finn et al.
2009/0265193 A1 10/2009 Collins et al.
2009/0281393 A1 11/2009 Smith
2009/0315735 A1 12/2009 Bhavani et al.
2009/0326981 A1 12/2009 Karkanias et al.
2010/0017718 A1 1/2010 Bohms
2010/0145164 A1 6/2010 Howell
2010/0191824 A1 7/2010 Lindsay
2010/0198608 A1 8/2010 Kaboff et al.
2010/0222649 A1 * 9/2010 Schoenberg ........... G16H 40/67 705/2
2010/0286490 A1 11/2010 Koverzin
2011/0021140 A1 1/2011 Binier
2011/0125844 A1 5/2011 Collier et al.
2011/0181422 A1 7/2011 Tran
2011/0201901 A1 8/2011 Khanuja
2011/0224501 A1 9/2011 Hudsmith
2011/0246123 A1 10/2011 DelloStritto et al.
2012/0095846 A1 4/2012 Leverant
2012/0143619 A1 6/2012 Routt
2012/0191788 A1 7/2012 Mellen
2012/0197662 A1 8/2012 Sun et al.
2012/0280811 A1 11/2012 McKalip
2012/0284040 A1 11/2012 Dupin
2012/0284637 A1 11/2012 Boyer et al.
2013/0035946 A1 * 2/2013 Ratan ..................... G16H 40/67 705/2
2013/0065569 A1 3/2013 Leipzig
2013/0073299 A1 3/2013 Warman et al.
2013/0073306 A1 3/2013 Shlain et al.
2013/0080209 A1 * 3/2013 Begeja ................... G06Q 40/12 705/7.32
2013/0082842 A1 4/2013 Balazs et al.
2013/0095459 A1 4/2013 Tran
2013/0100268 A1 4/2013 Mihailidis et al.
2013/0110895 A1 5/2013 Valentino et al.
2013/0147899 A1 6/2013 Labhard
2013/0148942 A1 6/2013 Ryan et al.
2013/0262155 A1 10/2013 Hinkamp
2013/0267795 A1 10/2013 Cosentino et al.
2014/0052474 A1 2/2014 Madan et al.
2014/0074454 A1 3/2014 Brown et al.
2014/0108031 A1 4/2014 Ferrara
2014/0129160 A1 5/2014 Tran
2014/0136264 A1 5/2014 Kinsey, II
2014/0148733 A1 5/2014 Stone et al.
2014/0188997 A1 7/2014 Schneiderman et al.
2014/0207486 A1 7/2014 Carty et al.

(56) References Cited

U.S. PATENT DOCUMENTS

2014/0257851 A1 9/2014 Walker et al.
2014/0266669 A1 9/2014 Fadell et al.
2014/0266791 A1 9/2014 Lloyd
2014/0284348 A1 9/2014 Cheng
2014/0362213 A1 12/2014 Tseng
2015/0002293 A1 1/2015 Nepo
2015/0006200 A1 1/2015 Chaput et al.
2015/0020170 A1 1/2015 Talley
2015/0077237 A1 3/2015 Chou et al.
2015/0094144 A1 4/2015 Brown et al.
2015/0094830 A1 4/2015 Lipoma et al.
2015/0134343 A1 5/2015 Kluger et al.
2015/0154880 A1 6/2015 Petito et al.
2015/0179040 A1 6/2015 Nishihara
2015/0194032 A1 7/2015 Wright
2015/0213224 A1 7/2015 Amarasingham et al.
2015/0223705 A1* 8/2015 Sadhu ................ G08B 21/0453 600/595
2015/0269329 A1 9/2015 Fearon et al.
2015/0288797 A1 10/2015 Vincent
2015/0302538 A1 10/2015 Mazar et al.
2015/0312740 A1 10/2015 Li et al.
2015/0356701 A1 12/2015 Gandy et al.
2016/0026354 A1 1/2016 Mcintosh
2016/0027278 A1 1/2016 Mcintosh
2016/0086255 A1 3/2016 Sainfort et al.
2016/0110509 A1 4/2016 Girardeau
2016/0140320 A1 5/2016 Moturu et al.
2016/0155163 A1* 6/2016 White ................ G06Q 30/0611 705/26.2
2016/0171864 A1 6/2016 Ciaramelletti et al.
2016/0174913 A1 6/2016 Somanath et al.
2016/0203444 A1 7/2016 Frank et al.
2016/0210427 A1* 7/2016 Mynhier ................ G16H 10/60
2016/0210434 A1 7/2016 Al-Sharif
2016/0214571 A1 7/2016 Othmer et al.
2016/0225240 A1 8/2016 Voddhi et al.
2016/0246936 A1* 8/2016 Kahn ..................... G16H 40/63
2016/0259902 A1 9/2016 Feldman et al.
2016/0314514 A1 10/2016 High et al.
2016/0342767 A1* 11/2016 Narasimhan ............ G16Z 99/00
2016/0350721 A1 12/2016 Comerford et al.
2016/0371620 A1 12/2016 Nascenzi et al.
2017/0004273 A1 1/2017 Mbanefo et al.
2017/0004695 A1 1/2017 Brasch
2017/0011188 A1 1/2017 Arshad et al.
2017/0011195 A1* 1/2017 Arshad .................. G16H 30/20
2017/0024525 A1 1/2017 Walker
2017/0046501 A1 2/2017 Coleman et al.
2017/0094057 A1 3/2017 Naiga et al.
2017/0116384 A1 4/2017 Ghani
2017/0124276 A1 5/2017 Tee
2017/0124277 A1 5/2017 Shlagman
2017/0124526 A1 5/2017 Sanderford et al.
2017/0193164 A1 7/2017 Simon et al.
2017/0214758 A1 7/2017 Engel
2017/0228109 A1 8/2017 Zhang et al.
2017/0262604 A1 9/2017 Francois
2017/0270260 A1 9/2017 Shetty et al.
2017/0277834 A1 9/2017 Zipnick et al.
2017/0293878 A1 10/2017 Donnelly et al.
2017/0300626 A1* 10/2017 Love ................ G06Q 10/06311
2018/0007131 A1 1/2018 Cohn
2018/0032696 A1 2/2018 Rome
2018/0068081 A1 3/2018 Salem
2018/0075204 A1 3/2018 Lee et al.
2018/0082184 A1 3/2018 Guo
2018/0153477 A1 6/2018 Nagale et al.
2018/0158548 A1 6/2018 Taheri et al.
2018/0177436 A1* 6/2018 Chang .................. A61B 5/1117
2018/0182055 A1 6/2018 Jepson et al.
2018/0194919 A1 7/2018 Wu
2018/0196919 A1 7/2018 Abou Mahmoud
2018/0211509 A1 7/2018 Ramaci
2018/0211724 A1 7/2018 Wang
2018/0276710 A1 9/2018 Tietzen et al.
2018/0280245 A1 10/2018 Khalid
2018/0308569 A1 10/2018 Luellen
2018/0315499 A1 11/2018 Appelbaum et al.
2018/0322469 A1 11/2018 Logtenberg
2018/0322947 A1 11/2018 Potts et al.
2018/0325470 A1 11/2018 Fountaine
2018/0336048 A1 11/2018 Zarlengo et al.
2018/0342329 A1* 11/2018 Rufo ..................... G16H 40/67
2018/0344215 A1* 12/2018 Ohnemus ............. A61B 5/1118
2018/0357386 A1 12/2018 Sanjay-Gopal
2018/0365957 A1 12/2018 Wright et al.
2019/0046039 A1 2/2019 Ramesh et al.
2019/0069154 A1 2/2019 Booth et al.
2019/0080056 A1 3/2019 Das
2019/0083003 A1 3/2019 Lee et al.
2019/0108841 A1 4/2019 Vergyri et al.
2019/0122522 A1 4/2019 Stefanski
2019/0122760 A1* 4/2019 Wang ..................... G16H 10/60
2019/0133445 A1 5/2019 Eteminan et al.
2019/0156944 A1 5/2019 Eriksson
2019/0180868 A1* 6/2019 Makram ................ G16H 10/60
2019/0182299 A1* 6/2019 O'Brien .................. H04L 63/12
2019/0198169 A1* 6/2019 T ............................ G16H 50/50
2019/0205675 A1 7/2019 McGill
2019/0206533 A1 7/2019 Singh et al.
2019/0213557 A1 7/2019 Dotan-Cohen et al.
2019/0279116 A1 9/2019 Caligor
2019/0279647 A1 9/2019 Jones et al.
2019/0287376 A1 9/2019 Netscher et al.
2019/0287676 A1 9/2019 Kaplan et al.
2019/0318283 A1 10/2019 Kelly
2019/0319813 A1 10/2019 Abu-Ghazaleh
2019/0320900 A1 10/2019 Majmudar
2019/0325502 A1* 10/2019 Tovey ................ G06Q 30/0635
2019/0334907 A1 10/2019 Rodden et al.
2019/0362319 A1 11/2019 Yen
2019/0388017 A1* 12/2019 Keating ................. G16H 40/67
2019/0392489 A1 12/2019 Tietzen et al.
2020/0005928 A1* 1/2020 Daniel ................... G16H 15/00
2020/0019852 A1 1/2020 Yoon et al.
2020/0020165 A1 1/2020 Tran
2020/0020454 A1* 1/2020 McGarvey ......... G06Q 30/0282
2020/0043077 A1 2/2020 Turner et al.
2020/0058381 A1* 2/2020 Patel ...................... G16H 10/60
2020/0074382 A1* 3/2020 Olsen ..................... G16H 40/67
2020/0121544 A1 4/2020 George et al.
2020/0126670 A1 4/2020 Bender et al.
2020/0143655 A1 5/2020 Gray et al.
2020/0160428 A1 5/2020 Calvo et al.
2020/0302549 A1 9/2020 Jordan et al.
2020/0312113 A1 10/2020 Victor
2020/0327791 A1 10/2020 Moon et al.
2020/0335183 A1 10/2020 Tommasi et al.
2020/0341593 A1 10/2020 Han et al.
2020/0349632 A1 11/2020 Xu et al.
2020/0365264 A1 11/2020 Girardeau et al.
2021/0019694 A1 1/2021 Dhesi et al.
2021/0035432 A1 2/2021 Moon et al.
2021/0042843 A1 2/2021 Bryant et al.
2021/0043058 A1 2/2021 Williams et al.
2021/0158671 A1 5/2021 Jordan et al.
2021/0335115 A1 10/2021 Williams et al.
2021/0358618 A1 11/2021 Crocker
2022/0031239 A1 2/2022 Curtis
2022/0159344 A1 5/2022 Gutierrez
2022/0310079 A1 9/2022 Kalns et al.
2022/0355802 A1 11/2022 Chaves

FOREIGN PATENT DOCUMENTS

JP 2002092767 A 3/2002
JP 2006048554 A 2/2006
JP 2013179381 A 9/2013
JP 2014056423 A 3/2014
JP 2014142889 A 8/2014
JP 2017116994 A 6/2017
JP 2017215971 A 12/2017
WO 2009061936 A1 5/2009

(56) References Cited

FOREIGN PATENT DOCUMENTS

| | | | |
|---|---|---|---|
| WO | 2011133628 | A1 | 10/2011 |
| WO | 2014106294 | A1 | 7/2014 |
| WO | 2019086849 | A1 | 5/2019 |
| WO | 2019246239 | A1 | 12/2019 |
| WO | 2020010217 | A1 | 1/2020 |

OTHER PUBLICATIONS

S. A. Becker and F. Webbe, "Use of Handheld Technology by Older Adult Caregivers as Part of a Virtual Support Network," 2006 Pervasive Health Conference and Workshops, 2006, pp. 1-10, doi: 10.1109/PCTHEALTH.2006.361697.

E. Leinonen, A. Firouzian, C. Partanen and P. Pulli, "Visual validation services with time coordination for senior citizens social events—OldBirds digital twin platform," 2019 IEEE International Conference on Engineering, Technology and Innovation (ICE/ITMC), 2019, pp. 1-7, doi: 10.1109/ICE.2019.8792663.

"Elderly Alexa helps families care for their loved ones via voice", Perez, Sarah, techcrunch.com, May 14, 2017 (Year: 2017).

"How to use Alexa Care Hub to help monitor and contact older relatives or friends", Dave Johnson, Business Insider, Jan. 14, 2021, https://www.businessinsider.com/how-to-use-alexa-care-hub.

Amazons Care Hub will see success due to swelling interest in aging at home and boosted smart speaker adoption, Zoe LaRock, Nov. 13, 2020, https://www.businessinsider.com/amazon-care-hub-will-succeed-amid-growing-smart-speaker-adoption-2020-11.

Apple. (Dec. 17, 2018). SilverSneakers GO. Retrieved from Itunes App Store: https://itunes.apple.com/us/app/silversneakers-go/id1410437380mt=8.

Apple. (Dec. 6, 2018). App Store. Retrieved from Apple Web Site: https://www.apple.com/ios/app-store/.

Apple. (Dec. 6, 2018). DVD Netflix. Retrieved from iTunes App Store Preview: https://itunes.apple.com/us/app/dvd-netflix/id1169772776mt=8.

Jeff Johnson, "Designing User Interfaces for an Aging Population", Feb. 2017 | Talks at Google. Retrieved from Youtube: https://www.youtube.com/watchv=czjksAESHAo, Abstract only.

Nunez-Marcos et al., Vision-based fall detection with convolutional neural networks, Wireless and Communications and Mobile Computing, vol. 2017, Article ID 9474806, 16 pgs.

Tesla. (Dec. 6, 2018). Discover Software Version 9.0. Retrieved from Tesla Corporation Website: https://www.tesla.com/support/software-v9.

The Accuracy Of Self-Reported Data Of An Aging Population Using A Telehealth System In A Retirement Community Setting Based On The Users Age, Gender, Employment Status And Computer Experience, Gurley, Kelley Anne. University of Maryland, Baltimore.

Yildirim et al., Fall detection using smartphone-based application, International Journal of Applied Mathmatics Electronics and Computers 4, No. 4, 2016.

Yu et al. A posture recognition-based fall detection system for monitoring an elderly person in a smart home environment, IEEE transactions on Information Technology in Biomedicine 16, No. 6: 1274-1286.

Pirzada et al., Sensors in Smart Homes for Independent Living of the Elderly, 2018, 2018 5th International Multi-Topic CT Conference (IMTIC) (Year: 2018).

S. Jiang, Y. Cao, S. Iyengar, P. Kuryloski, R. Jafari, Y. Xue, R. Bajcsy, S. Wicker. "CareNet: An Integrated Wireless Sensor Networking Environment for Remote Healthcare," Proceedings of the 3rd International Conference on Body Area Networks (Bodynets 2008), Mar. 13-15, 2008.

P. Kuryloski, S. Pai, S. Wicker, Y. Xue, "MedSN System for In-Home Patient Monitoring: Architecture, Privacy and Security" Proceedings of the Joint Conference on High Confidence Medical Devices, Software, and Systems (HCMDSS07) and Medical Device Plug-and-Play Interoperability (MD PnP07), Jun. 25-27, 2007, Boston, MA.

J. Anish Dev, "Bitcoin mining acceleration and performance quantification," 2014 IEEE 27th Canadian Conference on Electrical and Computer Engineering (CCECE), 2014, pp. 1-6 (Year: 2014).

C. R. Costa, L. E. Anido-RifOn and M. J. Fernandez-Iglesias, "An Open Architecture to Support Social and Health Services in a Smart TV Environment," in IEEE Journal of Biomedical and Health Informatics, vol. 21, No. 2, pp. 549-560, Mar. 2017, doi: 10.1109/JBHI.2016.2525725 (Year: 2017).

H. Wang, Q. Zhang, M. Ip and J. T. Fai Lau, "Social Media-based Conversational Agents for Health Management and Interventions," in Computer, vol. 51, No. 8, pp. 26-33, Aug. 2018, doi: 10.1109/MC.2018.3191249 (Year: 2018).

"Amazon Echo Silver—Saturday Night Live" video available at https://www.youtube.com/watchv=YvT_gqs5ETk, posted May 13, 2017.

"HoneyCo Connect" video available at https://fabricofdigitallife.com/Detail/objects/3488, posted Jul. 5, 2017.

HoneyCo Homes, "Caregiver Platform" video available at https://vimeo.com/240045919, posted 2017.

HoneyCo Homes, "Office Basic" video available at https://vimeo.com/250049021, posted 2018.

HoneyCo Homes, "Office Advanced" video available at https://vimeo.com/250049062, posted 2018.

HoneyCo Homes, "Office Basic" video available at https://vimeo.com/250126734, posted 2018.

HoneyCo Homes, "HoneyCo Advanced" video available at https://vimeo.com/250139424, posted 2018.

HoneyCo Homes Vimeo page retrieved from https://vimeo.com/honeycohomes on Jul. 3, 2023, 2p.

NBC 5, Dallas-Fort Worth, Feb. 23, 2004, video available at https://ailab.wsu.edu/mavhome/movies/MavPad_NBC5_2_23_2004.mov.

Amazon Echo Show Teardown video available at https://web.archive.org/web/20180130021123/ifixit.com/teardown/amazon+echo+show+teardown/94625, Jan. 30, 2018.

Meet Alexa: Reminders video available at https://www.youtube.com/shorts/v7ZmznZgxSY.

freeCodeCamp.org, Amazon Alexa Development 101 (full tutorial course—Jun. 2018 version) video available at https://www.youtube.com/watchv=QkbXjknPoXc.

Toms Guide, So Easy: How to Delete Alexas History video available at https://www.youtube.com/watchv=VvS9JOtv5e0, 2017.

HoneyCo Homes, "HoneyCo Connect" available at https://vimeo.com/224366987, posted 2017.

Zechmann et al., "Challenges in communicating user requirements: Lessons learned from a multi-national AAL project", International Reports on Socio-Informatics (IRSI), Proceedings of the COOP 2016—Symposium on challenges and experiences in designing for an ageing society, (vol. 13, Iss. 3, pp. 43-50), 8 p.

Jarvis, Jan, "The house that tech built—Buttons Push Themselves in Smart Texas Protoype and the Livin is easy" available at https://ailab.wsu.edu/mavhome/files/a1.5.02.jpg, Jan. 11, 2002, 2 p.

Su et al., "Radar placement for fall detection: Signature and performance", Journal of Ambient Intelligentce and Smart Environments, 2018, 10.3233/AIS-170469, 14 p.

Austin et al., "Variability in medication taking is associated with cognitive performance in nondemented older adults", Alzheimers and Dementia: Diagnosis, Assessment and Disease Monitoring, 2017, doi: 10.1016/j.dadm.2017.02.003. PMID: 28349120; PMCID: PMC5358531, 4 p.

Dawadi et al., "Automated Cognitive Health Assessment From Smart Home-Based Behavior Data", IEEE J Biomed Health Inform. Jul. 2016;20(4):1188-94. doi: 10.1109/JBHI.2015.2445754, PMID: 26292348; PMCID: PMC4814350, 38 p.

Austin et al., "A Smart-Home System to Unobtrusively and Continuously Assess Loneliness in Older Adults", IEEE Journal of Translational Engineering in Health and Medicine, 2016, doi: 10.1109/JTEHM.2016.2579638. PMID: 27574577; PMCID: PMC4993148, 11 p.

(56) References Cited

OTHER PUBLICATIONS

Borisov et al., "Measuring Changes in Gait and Vehicle Transfer Ability During Inpatient Rehabilitation with Wearable Inertial Sensors", Proc IEEE Int Conf Pervasive Comput Commun Workshops, Mar. 2017; 2017:10.1109/PERCOMW.2017.7917600. doi: 10.1109/PERCOMW.2017.7917600. PMID: 28691124; PMCID: PMC5497512, 25 p.
Canary Care How It Helps page retrieved from https://web.archive.org/web/20190322142707/canarycare.co.uk/how-it-helps/, Mar. 22, 2019, 10 p.
Canary Care How it works page retrieved from https://web.archive.org/web/20190322142414/https://www.canarycare.co.uk/how-it-works/, Mar. 22, 2019, 9 p.
Care Predict How it Works page retrieved from https://web.archive.org/web/20230627100828/https://www.carepredict.com/how-it-works/, Jan. 12, 2018, 6 p.
Curci et al., "Toward Naturalistic Self-Monitoring of Medicine Intake", In Proceedings of the 12th Biannual Conference on Italian SIGCHI Chapter (CHItaly 17), Association for Computing Machinery, New York, NY, USA, Article 3, 1-6. https://doi.org/10.1145/3125571.3125582, 6 p.
Care@Home Administrator User Guide retrieved from https://web.archive.org/web/20161109082617/essence-grp.com:80/data/upl/care_home_administrator_userguide.pdf, Jun. 2016, 117 p.
Care@Home PERS Control Panel User Guide retrieved from https://web.archive.org/web/20180413032733/http://www.essence-grp.com/data/upl/Care_Home_PERS_CP_UG.pdf, Sep. 2014, 38 p.
Essence Smart Care—Care@Home retrieved from https://web.archive.org/web/20161021001627/http://www.essence-grp.com/data/upl/resources/Essence%20Smart%20Care.pdf, retrieved Oct. 21, 2016, 6 p.
Fritz et al., "Identifying Varying Health States in Smart Home Sensor Data : An Expert-Guided Approach", 2017, 6 p.
Hellmers et al., "Towards a minimized unsupervised technical assessment of physical performance in domestic environments", In Proceedings of the 11th EAI International Conference on Pervasive Computing Technologies for Healthcare (PervasiveHealth 2017), Association for Computing Machinery, New York, NY, USA, 207-216. 10 p.
Su et al., "Monitoring the Relative Blood Pressure Using a Hydraulic Bed Sensor System", IEEE Transactions on Biomedical Engineering, vol. 66, No. 3, Mar. 2019, 740-748, doi: 10.1109/TBME.2018.2855639, PMID: 30010544, 9 p.
Banerjee et al., "Exploratory analysis of older adults" sedentary behavior in the primary living area using kinect depth data, Journal of Ambient Intelligence and Smart Environments, 9, 163-179, 10.3233/AIS-170428, 2017, 18 p.
Newland et al., "Continuous In-Home Symptom and Mobility Measures for Individuals With Multiple Sclerosis: A Case Presentation", Journal of Neuroscience Nurses, Aug. 2017; 49(4):241-246. doi: 10.1097/JNN.0000000000000299. PMID: 28661948. 6 p.
Lifepod Main page retrieved from https://web.archive.org/web/20180826082654/https://lifepod.com/, Aug. 26, 2018, 6 p.
Aicha et al., "Continuous Gait Velocity Analysis Using Ambient Sensors in a Smart Home", 219-235. 10.1007/978-3-319-26005-1_15, 2015, 17 p.
Seelye et al., "Passive Assessment of Routine Driving with Unobtrusive Sensors: A New Approach for Identifying and Monitoring Functional Level in Normal Aging and Mild Cognitive Impairment", Journal of Alzheimers Disease, 59, 10.3233/JAD-170116., 2017, 19 p.
Chung et al., "Feasibility testing of a home-based sensor system to monitor mobility and daily activities in Korean American older adults", Int J Older People Nurs. Mar. 2017;12(1). doi: 10.1111/opn.12127. PMID: 27431567. 31 p.
Petersen et al., "Time Out-of-Home and Cognitive, Physical, and Emotional Wellbeing of Older Adults: A Longitudinal Mixed Effects Model", PLoS One. Oct. 5, 2015;10(10): e0139643. doi: 10.1371/journal.pone.0139643. PMID: 26437228; PMCID: PMC4593630. 16 p.
Rantz et al., "Randomized Trial of Intelligent Sensor System for Early Illness Alerts in Senior Housing", J Am Med Dir Assoc. Oct. 1, 2017;18(10):860-870. doi: 10.1016/j.jamda.2017.05.012. Epub Jul. 12, 2017. PMID: 28711423; PMCID: PMC5679074. 28 p.
Riboni et al., "Fine-grained recognition of abnormal behaviors for early detection of mild cognitive impairment," 2015 IEEE International Conference on Pervasive Computing and Communications (PerCom), St. Louis, MO, USA, 2015, pp. 149-154, doi: 10.1109/PERCOM.2015.7146521. 10 p.
Robben et al. (2016). Delta Features From Ambient Sensor Data are Good Predictors of Change in Functional Health. IEEE Journal of Biomedical and Health Informatics. 21. 1-1. 10.1109/JBHI.2016.2593980. 8 p.
Robben et al. (2012). How Is Grandma Doing Predicting Functional Health Status from Binary Ambient Sensor Data. AAAI Fall Symposium: Artificial Intelligence for Gerontechnology. 6 p.
Robben et al. (2014). Expert knowledge for modeling the relation between functional health and data from ambient assisted living sensor systems. Poster session presented at 10th Congress of the European Union of Geriatric Medicine Society (EUGMS) 2014, Rotterdam. https://www.thieme-connect.com/products/ejournals/abstract/10.3414/ME15-01-0072, 1 p.
Sprint et al. (2016). Using Smart Homes to Detect and Analyze Health Events. Computer. 49. 29-37. 10.1109/MC.2016.338. 12 p.
Sprint et al. Analyzing Sensor-Based Time Series Data to Track Changes in Physical Activity during Inpatient Rehabilitation. Sensors (Basel). Sep. 27, 2017;17(10):2219. doi: 10.3390/s17102219. PMID: 28953257; PMCID: PMC5677114. 20 p.
Edison et al. (2017). Challenges and Opportunities in Automated Detection of Eating Activity. In: Rehg, J., Murphy, S., Kumar, S. (eds) Mobile Health. Springer, Cham. 24 p.
TruSense description page retrieved from https://web.archive.org/web/20170919160359/https://mytrusense.com/how-it-works, 2017, 9 p.
TruSense main page retrieved from https://web.archive.org/web/20180422211851/https://mytrusense.com/, 2018, 12 p.
Akl et al. Unobtrusive Detection of Mild Cognitive Impairment in Older Adults Through Home Monitoring. IEEE J Biomed Health Inform. Mar. 2017;21(2):339-348. doi: 10.1109/JBHI.2015.2512273. Epub Dec. 24, 2015. PMID: 26841424; PMCID: PMC4919247. 22 p.
Wang et al. Performance-based physical function and future dementia in older people. Arch Intern Med. May 22, 2006;166(10):1115-20. doi: 10.1001/archinte.166.10.1115. PMID: 16717174. 6 p.
Zanthion Environmental Sensors page retrieved from https://web.archive.org/web/20180711114243/http://www.zanthion.com/environment-sensors-notification/, retrieved 2018, 4 p.
Zanthion Smart Motion sales page retrieved from https://web.archive.org/web/20190128004506/https://zanthion.com/product/smart-motion/, retrieved 2018, 1 p.
Pullen, John Patrick. This Amazon Echo Tip Is Great for Families and Roommates. TIME, Feb. 13, 2017. retrieved from https://fortune.com/2017/02/13/amazon-echo-alexa-tips/ 6 p.
Amazon Echo Show Teardown available at https://web.archive.org/web/20180130021123/ifixit.com/teardown/amazon+echo+show+teardown/94625, Jan. 28, 2017, 11 p.
Gonfalonieri, Alexandre. How Amazon Alexa works Your guide to Natural Language Processing (Al) Towards Data Science, Nov. 21, 2018 17 p.
Ralevic, Uros. How to build a custom Amazon Alexa skill, step-by-step: My favorite chess player. Crowdbiotics. Jul. 24, 2018. 28 p.
Prospero, Mike. How to Create an Alexa Smart Home Routine. Toms Guide. Mar. 1, 2019. 19 p.
Newman, Jared. How to use Alexa Routines to make your Amazon Echo event smarter, TechHive. Dec. 17, 2018. 9 p.
"Introducing Echo Show—Black" sales page retrieved from https://web.archive.org/web/20170623020018/https://www.amazon.com/Amazon-MW46WB-Introducing-Echo-Show/dp/B01J24C0TI 1 p.
Amazon Echo Show Teardown available at https://web.archive.org/web/20180130021123/ifixit.com/teardown/amazon+echo+show+teardown/94625 10 p.

(56) References Cited

OTHER PUBLICATIONS

PubNub, “4 Game Changers from the TechCrunch Disrupt Hackathon”, May 15, 2017, 15 p.
Marscarenhas, Natasha, “BostonInno Approved: The Week's Top Tech & Startup Events in Boston”, Mar. 17, 2017, 5 p.
“Elderly-Alexa”, TechCrunch video retrieved from https://techcrunch.com/unified-video/elderly-alexa/, May 14, 2017, 12 p.
“Facilitating Elders Aging in Place: The 2017 Enterprise Management Hackathon”, retrieved from https://mitsloan.mit.edu/sites/default/files/inline-files/2017_EMTrack_Hackathon_article.pdf.
“Elderly Alexa' helps families care for their remote loved ones via voice”, reposted by Northeastern Global News, May 14, 2017, 3 p.
“Elderly-Alexa” TechCrunch article retrieved from https://techcrunch.com/unified-video/elderly-alexa/, May 14, 2017, 7 p.
Perez, Sarah, ‘Elderly Alexa' helps families care for their remote loved ones via voice, TechCrunch, May 14, 2017, 8 p.
“Alexa: 1001 Tips and Tricks How To Use Your Amazon Alexa devices (Amazon Echo, Second Generation Echo, Echo Show, Amazon Echo Look, Echo Plus, Echo Spot, Echo Dot, Echo Tap, Echo Connect)” sales page retrieved from https://www.amazon.com/alexa-tricks-devices-generation-connect/dp/1981989463 on Jul. 6, 2023, 7 p.
“Amazon Echo Show: 2018 Updated Advanced User Guide to Amazon Echo Show with Step-by-Step Instructions (alexa, dot, echo user guide, echo amazon, amazon dot, echo show, user manual)” sales page retrived from https://www.amazon.com/amazon-echo-show-step-step/dp/1986412385 on Jun. 28, 2023, 6 p.
“Amazon.com: Echo Show—1st Generation White : Amazon Devices Accessories” sales page retrieved from https://www.amazon.com/Amazon-Echo-Show-Alexa-Enabled-White/dp/BO10CEHQTG/ref=cm_cr_arp_d_product_topie=UTF8 th=1 on Jun. 20, 2023, 10 p.
“Amazon Echo Quick Start Guide” retrieved from https://d1ergij2b6wmg5.cloudfront.net/Amazon_Echo_Quick_Start_Guide.pdf , retreived Aug. 16, 2023, 1 p.
“Echo Show | Alexa-enabled Bluetooth Speaker with 7" Screen—Black” sales page retrieved from https://web.archive.org/web/20180905034124/https://www.amazon.com/Amazon-Echo-Show-Alexa-Enabled-Black/dp/B01J24C0TI on Jun. 27, 2023, 22 p.
“Echo Show (2nd Generation) Quick Start Guide” retrived from https://d1ergij2b6wmg5.cloudfront.net/Alexa+Devices/ Echo+Show+(2nd+Generation)_QSG_US.pdf, retrieved Aug. 16, 2023, 1 p.
“Amazon Echo (Second Generation) Quick Start Guide” retrieved from https://d1ergij2b6wmg5.cloudfront.net/Alexa+Devices/Echo_(2nd+Generation)_QSG_US.pdf , retrieved Aug. 16, 2023, 1 p.
Fratu, Octavia, Martian, Alexandru, Lazaridis, Pavlos, Zaharis, Zaharias D. and Kasampalis, Stylianos (2015) Comparative study of Radio Mobile and ICS Telecom propagation prediction models for DVB-T. In: IEEE Bmsb 2015 International Conference, Jun. 17-19, 2015, Ghent, Belgium. 7 p.
“Introducing Echo Show—Black” sales page retrieved from the Wayback Machine at https://web.archive.org/web/20170623020018/https://www.amazon.com/Amazon-MW46WB-Introducing-Echo-Show/dp/B01J24C0TI on Jun. 23, 2023, 15 p.
“Quick Start Guides for Alexa-Enabled Devices” customer service page retrieved from https://www.amazon.com/gp/help/customer/display.htmlnodeld=202016340 on Jul. 2, 2023, 5 p.
Infarinato, F.; Jansen-Kosterink, S.; Romano, P.; van Velsen, L.; op den Akker, H.; Rizza, F.; Ottaviani, M.; Kyriazakos, S.; Wais-Zechmann, B.; Garschall, M.; et al. Acceptance and Potential Impact of the eWALL Platform for Health Monitoring and Promotion in Persons with a Chronic Disease or Age-Related Impairment. Int. J. Environ. Res. Public Health 2020, 17, 7893. 17 p.
Woyke, Elizabeth, “The Octogenarians Who Love Amazons Alexa”, MIT Technology Review, Jun. 9, 2017, 8 p.
“Alexa and Alexa Device FAQs” retrieved from https://web.archive.org/web/20171207040009/https://www.amazon.com/gp/help/customer/display.htmi/ref=hp_left_v4_sibie=UTF8 nodeid=201602230 on Dec. 7, 2017, 8 p.
“Echo Show” sales page retrieved from the Wayback Machine at https://web.archive.org/web/20170703150634/https://www.amazon.com/Amazon-Echo-Show-ALexa-Enabled-Black/dp/B01J24C0TI on Sep. 5, 2018, 1 p.
“Introducing Echo Show—Black” sales page retrieved from the Wayback Machine at https://web.archive.org/web/20230327065229/https://www.amazon.com/Amazon-MW46WB-Introducing-Echo-Show/dp/B01J24COTI on Jun. 23, 2017, 1 p.
Choi, Edward, et al. “Doctor Al: Predicting Clinical Events via Recurrent Neural Networks,” Proceedings of Machine Learning for Healthcare 2016, JMLR Workshop Conf Proc. Aug. 2016; 56: 301-318.
EWall for Active Long Living, Preliminary User and System Requirements, Deliverable D2.1 version 1 retrieved from https://cordis.europa.eu/docs/projects/cnect/8/610658/080/deliverables/001-eWALLD21v10.pdf , Feb. 26, 2014, 56 p.
EWall for Active Long Living, Initial Scenarios and Use-Cases, Deliverable D2.2 version 1 retrieved from https://cordis.europa.eu/docs/projects/cnect/8/610658/080/deliverables/001-eWALLD22v10.pdf , Feb. 28, 2014, 74 p.
EWall for Active Long Living, Ethics, Privacy and Security, Deliverable D2.4 version 1 retrieved from https://cordis.europa.eu/docs/projects/cnect/8/610658/080/deliverables/001-eWALLD24v10.pdf, Apr. 29, 2014, 32 p.
EWall for Active Long Living, Ethics, Clinical Workflows and Pathways, Deliverable D2.5 version 1 retrieved from https://cordis.europa.eu/docs/projects/cnect/8/610658/080/deliverables/001-eWALLD25v10.pdf , Jul. 30, 2014, 59 p.
EWall for Active Long Living, Evaluation and validation methodology, Deliverable D2.6 version 1.2 retrieved from https://cordis.europa.eu/docs/projects/cnect/8/610658/080/deliverables/001-eWALLD26v121.pdf , Oct. 31, 2014, 30 p.
EWall for Active Long Living, eWALL configurable metadata streams, Deliverable D3.3.1 version 1.0 retrieved from https://cordis.europa.eu/docs/projects/cnect/8/610658/080/deliverables/001-eWALLD331v10.pdf , Oct. 31, 2014, 27 p.
EWall for Active Long Living, eWALL configurable metadata streams, Deliverable D3.3.2 version 1.0 retrieved from https://cordis.europa.eu/docs/projects/cnect/8/610658/080/deliverables/001-eWALLD332v10.pdf , Apr. 29, 2015, 45 p.
EWall for Active Long Living, Technical evaluation report, Deliverable D6.3 version Final retrieved from https://cordis.europa.eu/docs/projects/cnect/8/610658/080/deliverables/001-eWALLD63v10.pdf , Apr. 30, 2015, 35 p.
EWall for Active Long Living, Technical evaluation report, Deliverable D6.3 version 1.1 retrieved from https://cordis.europa.eu/docs/projects/cnect/8/610658/080/deliverables/001-eWALLD63v11.pdf, Oct. 30, 2015, 68 p.
EWall for Active Long Living, Smale scale studies report, Deliverable D6.4 version 1.0 retrieved from https://cordis.europa.eu/docs/projects/cnect/8/610658/080/deliverables/001-eWALLD64v10.pdf, Oct. 31, 2015, 115 p.
EWall for Active Long Living, Socio-economic study, Deliverable D7.10 version 1.0 retrieved from https://cordis.europa.eu/docs/projects/cnect/8/610658/080/deliverables/001-eWALLD710v10.pdf , Oct. 31, 2016, 44 p.
EWall for Active Long Living, Website, Deliverable D7.1 version 1.0 retrieved from https://cordis.europa.eu/docs/projects/cnect/8/610658/080/deliverables/001-eWALLD71v10.pdf , Nov. 11, 2013, 9 p.
EWall for Active Long Living, Basic dishemination material, Deliverable D7.2 version 1.0 retrieved from https://cordis.europa.eu/docs/projects/cnect/8/610658/080/deliverables/001-eWALLD72v10.pdf, Dec. 16, 2013, 14 p.
EWall for Active Long Living, Disemination material, Deliverable D7.3 version 1.0 retrieved from https://cordis.europa.eu/docs/projects/cnect/8/610658/080/deliverables/001-eWALLD73v10.pdf , Jan. 31, 2014, 19 p.
EWall for Active Long Living, Standardization contributions, Deliverable D7.5.1 version 0.3 retrieved from https://cordis.europa.eu/docs/projects/cnect/8/610658/080/deliverables/001-eWALLD751v03.pdf , Oct. 31, 2015, 25 p.

(56) References Cited

OTHER PUBLICATIONS

EWall for Active Long Living, Standardization contributions, Deliverable D7.5.2 version 1.0 retrieved from https://cordis.europa.eu/docs/projects/cnect/8/610658/080/deliverables/001-eWALLD751v03.pdf , Oct. 31, 2016, 15 p.
EWall for Active Long Living, 1st Project Workshop, Deliverable D7.6.1 version 1.0 retrieved from https://cordis.europa.eu/docs/projects/cnect/8/610658/080/deliverables/001-eWALLD761v10.pdf , Oct. 31, 2014, 9 p.
EWall for Active Long Living, Education material training of professionals, Deliverable D7.7 version 1.0 retrieved from https://cordis.europa.eu/docs/projects/cnect/8/610658/080/deliverables/001-eWALLD77v10.pdf , Oct. 26, 2016, 70 p.
EWall for Active Long Living, Report on demonstration trial, Deliverable D8.3 version 2.3 retrieved from https://cordis.europa.eu/docs/projects/cnect/8/610658/080/deliverables/001-eWALLD83v23.pdf , Dec. 4, 2016, 104 p.
Schaarup, Clara Hangaard, Stine Hejlesen, Ole. (2016). Cognitive Walkthrough: An Element in System Development and Evaluation—Experiences From The eWALL Telehealth System. Procedia Computer Science. 100. 539-546. 10.1016/j.procs.2016.09.193.
Kyriazakos S, Valentini V, Cesario A, Zachariae R. Forecast—A cloud-based personalized intelligent virtual coaching platform for the well-being of cancer patients. Clin Transl Radiat Oncol. Nov. 21, 2017;8:50-59. doi: 10.1016/j.ctro.2017.11.006. PMID: 29594242; PMCID: PMC5862678.
Ichkov, Aleksandar Atanasovski, Vladimir Gavrilovska, Liljana. (2015). Hybrid access control with modified SINR association for future heterogeneous networks. 5 p.
2nd AHA Summit retrieved from https://web.archive.org/web/20181129003943/http://cloudcare2u.com/2nd-aha-summit/ on May 31, 2023, 5 p.
Bouwer, Julia. Evaluating eWALL: Assessing and enhancing older adults acceptance of a protoype smart home technology, Jan. 2015, retrieved from https://essay.utwente.nl/69042/1/Bouwer_BA_BMS.pdf , 59 p.
Lumini, Maria Jose, Fatima Araujo, and Teresa Martins. 2018. "The Role of Educational Technology in Caregiving". Caregiving and Home Care. InTech. doi: 10.5772/intechopen.72887 25 p.
EWALL Twitter page retrieved from https://twitter.com/eWALLproject on May 31, 2023, 10 p.
EWALL OSS—CloudCare2U page retrieved from https://web.archive.org/web/20181129004010/http://cloudcare2u.com/ewall/ on May 31, 2023, 2 p.
EWALL Project—Github page retrieved from https://github.com/ewallprojecteu on May 31, 2023, 2 p.
EWALL: An Open-Source Cloud-Based eHealth Platform for Creating Home Caring Environments for Older Adults Living with Chronic Diseases or Frailty—coversheet at https://link.springer.com/article/10.1007/s11277-017-4656-7, 2017, 2 p.
Kyriazakos, S., Prasad, R., Mihovska, A. et al. eWALL: An Open-Source Cloud-Based eHealth Platform for Creating Home Caring Environments for Older Adults Living with Chronic Diseases or Frailty. Wireless Pers Commun 97, 1835-1875 (2017). 65 p.
Pradhan et al. ; "Accessibility Came by Accident'—Use of Voice-Controlled Intelligent Personal Assistants by People with Disabilities." Proceedings of the 2018 CHI Conference on human factors in computing systems; 2018.
Parde, Natalie; Reading with Robots: A Platform to Promote Cognitive Exercise Through Identification and Discussion of Creative Metaphor in Books; : University of North Texas. ProQuest Dissertations Publishing, 2018. 11005488. (Year: 2018)
Riboni et al., "Extended Report: Fine-grained recognition of abnormal behaviors for early detection of mild cognitive impairment," 2015 IEEE International Conference on Pervasive Computing and Communications (PerCom), St. Louis, MO, USA, 2015, pp. 149-154, doi: 10.1109/PERCOM.2015.7146521. 10 p.
Dawadi et al., "Automated Clinical Health Assessment From Smart Home-Based Behavior Data", IEEE J Biomed Health Inform. Jul. 2016;20(4): 1188-94. doi: 10.1109/JBHI.2015.2445754, PMID: 26292348; PMCID: PMC4814350, 38 p.
Alpaydin, Ethem "Introduction to Machine Learning" (3d ed. 2014) 640 p.
"Amazon Introduces the Alexa Skills Kit—A Free SDK for Developers," available at https://press.aboutamazon.com/2015/6/amazon-introduces-the-alexa-skills-kit-a-free-sdk-for-developers; Jun. 25, 2015; 7 pp.
"Announcing New Alexa Skills Kit (ASK) Features: Account Linking and Service Simulator," available at https://developer.amazon.com/en-US/blogs/alexa/post/Tx7MF6PV44SOXU/announcing-new-alexa-skills-kit-ask-features-account-linking-and-service-simulato.html; Sep. 4, 2015; 3 pp.
"2015 Year in Review: More than 130 Skills On Alexa [Infographic]," available at https://developer.amazon.com/en-US/blogs/alexa/post/Tx2V9VQZDG9IXX/2015-year-in-review-more-than-130-skills-on-alexa-infographi.html; Jan. 7, 2016; 2 pp.
"Amazon Announces HIPAA-Compliant Alexa Skills, Opening Possibilities for Senior Living," available at https://seniorhousingnews.com/2019/04/04/amazon-announces-hipaa-compliant-alexa-skills-opening-possibilities-for-senior-living/; Apr. 4, 2019; 4 pp.
"Ask My Buddy," available at https://www.amazon.com/Beach-Dev-Ask-My-Buddy/dp/B017YAF22Y; 2 pp.
"OnGuardian Wins Top Prize," available at https://www.onguardian.io/test-post/; 1 p.
"OnGuardian Selected as Finalist at Aging2.0 Global Startup Search," available at https://www.onguardian.io/new-post/; 2 pp.
"Exciting Update: Unveiling Our Latest Video Overview of OnGuardian for Communities!"; available at https://www.onguardian.io/category/news/; 1 p.
OnGuardian by OnGuardian Apps LLC; https://www.amazon.com/OnGuardian-Apps-LLC/dp/B06XGTJ549; 3 pp.
User Guide-Registration and Setup; https://www.onguardian.io/new-post-2/; 2 pp.
"Exciting Update: Unveiling Our Latest Video Overview of OnGuardian for Communities!"; available at https://www.onguardian.io/exciting-update-unveiling-our-latest-video-overview-of-onguardian-for-communities/; 6 pp.
Marcelino I, Lopes D, Reis M, Silva F, Laza R, Pereira A. Using the eServices platform for detecting behavior patterns deviation in the elderly assisted living: a case study. Biomed Res Int. 2015;2015:530828. doi: 10.1155/2015/530828. Epub Mar. 2, 20152. PM ID: 25874219; PMCID: PMC4385593. (Year: 2015).

* cited by examiner

MULTI-SIDED MATCH MAKING PLATFORMS

CROSS-REFERENCE TO RELATED APPLICATIONS

This application claims the benefit of priority to U.S. Provisional Patent Application Ser. No. 62/870,528, filed Jul. 3, 2019, entitled "MULTI-SIDED MATCH MAKING PLATFORMS," the entire contents and disclosures of which are hereby incorporated herein by reference in its entirety.

FIELD OF THE INVENTION

The present disclosure relates to multi-sided platforms and, more particularly, to systems and methods for using a multi-sided platform to make matches based upon a person's determined needs.

BACKGROUND

At least some conventional computer networks (e.g., matching platforms) have enabled consumers to be matched with providers. However, conventional systems usually merely match consumers with providers (e.g., one-sided platforms or two-sided platforms), and may not provide additional functionality. Further, in the known systems, consumers may have to determine a specific need before being matched with a provider. Known systems may have other drawbacks as well.

BRIEF SUMMARY

The present embodiments may relate to systems and methods for electronically determining one or more needs of a user and matching the user to providers based upon the determined needs. The system may include a multi-sided match making computing device, one or more third party servers, one or more client devices, one or more sensor servers, and/or one or more databases.

In one aspect, a multi-sided match making ("MMM") computer system for matching consumers to providers is provided, and the MMM computer system includes at least one processor in communication with at least one memory device. The at least one processor may be configured to: (i) receive registration data from a user, (ii) receive user data from at least one of a sensor and a mobile device associated with the user, wherein the user data is generated by the at least one of the sensor and the mobile device in response to an action carried out by the user, (iii) analyze the registration data and the user data, (iv) determine a need based upon the analyzed registration and user data, (v) transmit the determined need to at least one caregiver associated with the user, and/or (vi) match the user to at least one provider based upon the determined need, wherein the provider is at least one of the caregiver, another caregiver, and a service, and wherein the provider is able to meet the determined need for the user. The MMM computer system may include additional, less, or alternate functionality, including that discussed elsewhere herein.

In another aspect, a computer-implemented method for matching consumers to providers using a multi-sided match making ("MMM") computer system including at least one processor in communication with at least one memory device is provided. The method may include: (i) receiving registration data from a user, (ii) receiving user data from at least one of a sensor and a mobile device associated with the user, wherein the user data is generated by the at least one of the sensor and the mobile device in response to an action carried out by the user, (iii) analyzing the registration data and the user data, (iv) determining a need based upon the analyzed registration and user data, (v) transmitting the determined need to at least one caregiver associated with the user, and/or (vi) matching the user to at least one provider based upon the determined need, wherein the provider is at least one of the caregiver, another caregiver, and a service, and wherein the provider is able to meet the determined need for the user. The method may include additional, less, or alternate actions, including those discussed elsewhere herein.

In yet another aspect, at least one non-transitory computer-readable media having computer-executable instructions thereon, wherein when executed by at least one processor of a multi-sided match making ("MMM") computer system causes the at least one processor of the MMM computer system to: (i) receive registration data from a user, (ii) receive user data from at least one of a sensor and a mobile device associated with the user, wherein the user data is generated by the at least one of the sensor and the mobile device in response to an action carried out by the user, (iii) analyze the registration data and the user data, (iv) determine a need based upon the analyzed registration and user data, (v) transmit the determined need to at least one caregiver associated with the user, and/or (vi) match the user to at least one provider based upon the determined need, wherein the provider is at least one of the caregiver, another caregiver, and a service, and wherein the provider is able to meet the determined need for the user. The instructions may direct additional, less, or alternate functionality, including that discussed elsewhere herein.

BRIEF DESCRIPTION OF THE DRAWINGS

The Figures described below depict various aspects of the systems and methods disclosed therein. It should be understood that each Figure depicts an embodiment of a particular aspect of the disclosed systems and methods, and that each of the Figures is intended to accord with a possible embodiment thereof. Further, wherever possible, the following description refers to the reference numerals included in the following Figures, in which features depicted in multiple Figures are designated with consistent reference numerals.

There are shown in the drawings arrangements which are presently discussed, it being understood, however, that the present embodiments are not limited to the precise arrangements and are instrumentalities shown, wherein.

Figure 1:
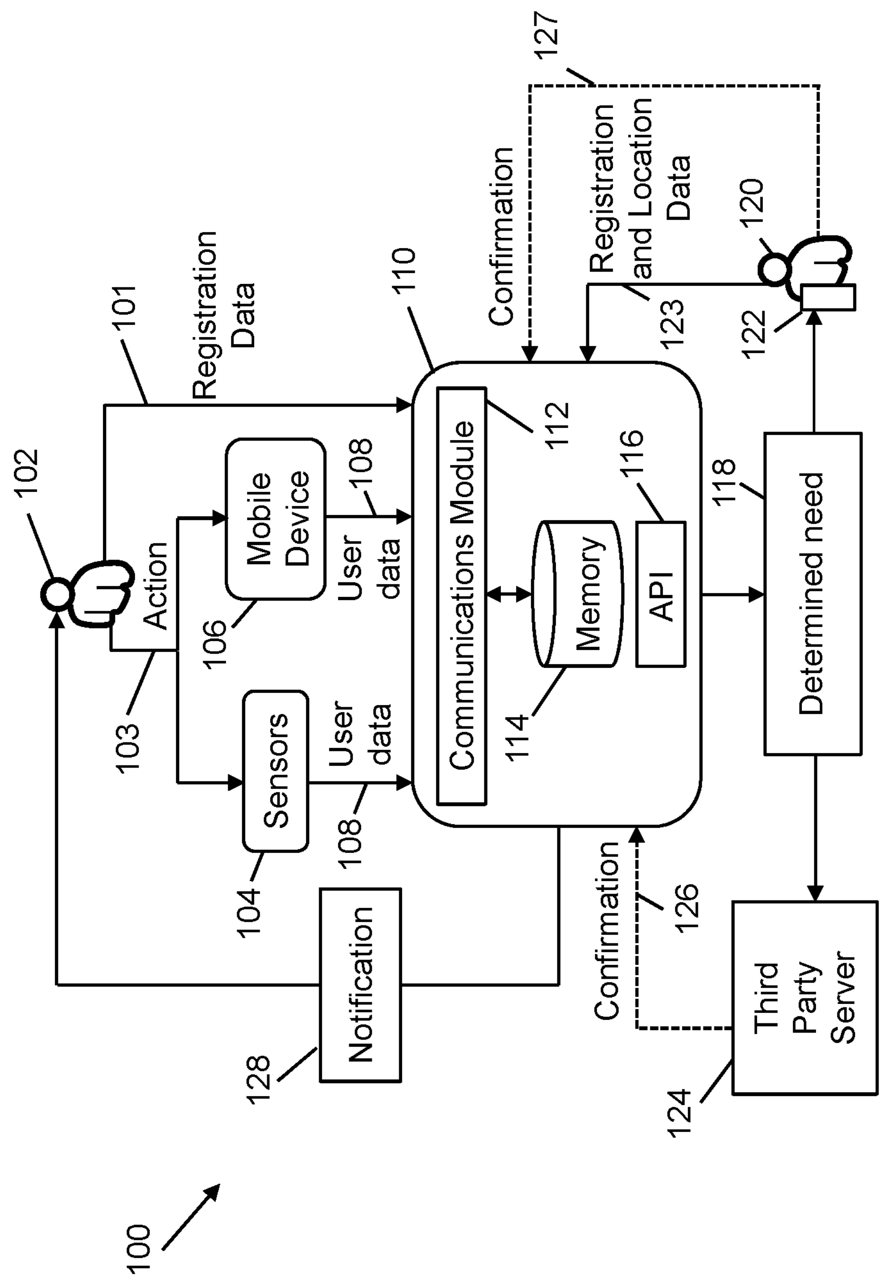
FIG. 1 illustrates a flow chart of an exemplary process of matching users to providers for a multi-sided match making system.

The Figures depict preferred embodiments for purposes of illustration only. One skilled in the art will readily recognize from the following discussion that alternative embodiments of the systems and methods illustrated herein may be employed without departing from the principles of the invention described herein.

DETAILED DESCRIPTION

The present embodiments may relate to, inter alia, systems and methods for electronically determining one or more needs of a user and matching the user to one or more providers based upon the determined needs of the user. In one exemplary embodiment, the process may be performed by a multi-sided match making ("MMM") computer system (also referred to herein as a "MMM platform" and a "MMM server"). In another embodiment, the process may be performed by a multi-sided caregiver platform ("MSCP") computer system, which may be configured to perform steps that are substantially similar to those described herein for the MMM computer system (e.g., the MMM computer system may include functionality substantially similar to the functionality of the MSCP computer system).

As described below, the systems and methods described herein may leverage sensor and mobile device data to determine a need of a user and match the user to one or more providers (e.g., caregivers and/or services) able to take care of the determined need for the user. The systems and methods described herein may learn the needs of the user such that the systems and methods described herein may automatically make arrangements with an appropriate one of the providers on behalf of the user without the user specifically initiating the process of having a need met. In some embodiments, the user may be a senior user who needs extra help going about his or her daily routine (e.g., rides to appointments, refills on their prescriptions, monitoring of activity, and completion of tasks, like taking their medicine). Caregivers (e.g., family members, friends, healthcare professionals, etc.) of the user may not be able to help the user every day, and friction between different caregivers may result if one or more caregivers help the user more often than other caregivers. Accordingly, the systems and methods described herein ensure that the needs of the users are met with little input from the user, and may reduce friction between different caregivers by effectively matching the user with the provider who is best able to take care of the user's determined need.

Exemplary User Data Collection

In the exemplary embodiment, a multi-sided match making ("MMM") service (e.g., provided by a multi-sided match making server) may leverage user data (e.g., sensor data, mobile device data, and registration data) to determine the needs of a user, match the user to one or more providers, and/or automatically make arrangements with the providers for the user. In the exemplary embodiment, the user may register for the multi-sided match making service provided by a multi-sided match making ("MMM") server through a mobile device associated with the user (e.g., through a multi-sided match making application on the mobile device) or through any other suitable device. As the user registers for the MMM service, the user may provide registration data to the MMM server for the MMM server to store in a memory device associated with the MMM server. Registration data may include, for example, age, birthdate, height, weight, medical history, preferred providers, and any other data associated with the user.

Further, in the exemplary embodiment, the user may enable the MMM server to receive data from servers associated with sensors that are associated with the user. For example, sensors may include mobile device sensors (e.g., GPS, speakers, and microphone), smart home device sensors (e.g., AMAZON ALEXA®, GOOGLE HOME®, NEST® devices, and RING® devices) (AMAZON, ALEXA, and RING are registered trademarks of Amazon Technologies, Inc., Seattle, Washington) (GOOGLE HOME is a registered trademark of Google, LLC. Mountain View, California) (NEST is a registered trademark of Nest Labs, Inc., Paulo Alto, California), and wearable device sensors (e.g., FITBIT® and APPLE WATCH®) (FITBIT is a registered trademark of Fitbit, LLC., San Francisco, California) (APPLE WATCH is a registered trademark of Apple, Inc., Cupertino, California). Sensors may also include autonomous vehicle sensors, smart vehicle sensors, and/or other vehicle sensors relating to telematics (e.g., cornering, braking, acceleration, etc.) of a vehicle, and the sensors may be directly coupled to the vehicle (e.g., back-up cameras, proximity sensors, etc.), and/or associated with the mobile device (e.g., sensors, including GPS, accelerometers, gyroscopes, etc., associated with a mobile telematics application) when the vehicle is being driven. Sensors may also be smart infrastructure sensors (e.g., streetlight, street, and traffic sensors), and/or smart building sensors (e.g., building cameras, building entrance/exit sensors, and utility sensors). The user may also enable the MMM server to receive data (e.g., notifications, reminders, and calendar data) from the mobile device of the user.

The data received by the MMM server from the sensors and/or the mobile device associated with the user may be considered user data, and the user data may be generated by the sensors and/or the mobile device in response to an action taken by the user when the user interacts with the sensor and/or the mobile device. Data from the sensors may include, for example, a GPS location of the user, conversations the user has over the mobile device or evidence of patterns of conversations without requiring verbatim collection of conversation content, questions the user asks the smart home device, driving scores and/or travel data from the vehicle and/or the mobile device, daily activity data, sleeping pattern data, movement data, physical condition data, and/or vital data from the wearable device, home utility/telematics data (e.g., gas, water, and electric usage and occupancy data) from the building and/or smart home device sensors, and any other data from sensors that may be useful to the MMM server in determining a need of the user. Data from the mobile device may include, for example, notifications sent to the user, third party application data (e.g., doctor and pharmacy applications relating to, for example, appointment scheduling and prescription refill scheduling), a calendar of the user, phone usage data (e.g., how often the phone is used and/or how many phone calls/text messages are sent out in a day), social media data (e.g., social interaction data and response times to messages/comments), and any other data from the mobile device that may be useful to the MMM server in determining a need of the user.

Once the user is registered and the MMM server is able to receive data from the sensors and the mobile device associated with the user, the MMM server may begin collecting and storing user data from the sensors and/or from the mobile device.

Exemplary Need and Abnormal Condition Determination

In the exemplary embodiment, the MMM server may analyze the received user and registration data to determine a need and/or an abnormal condition of the user. For example, if the user schedules a doctor's appointment on the mobile device associated with the user and the MMM server receives this scheduled appointment as user data from the mobile device, the MMM server may determine that the need for the user is that the user needs to get to the user's scheduled doctor's appointment. Further, the MMM server may analyze the registration data from the user and determine that the user is unable to drive. Thus, the MMM server may determine that the need for the user is a ride to their scheduled doctor's appointment.

To analyze the data, the MMM server may input the received user and registration data into a machine learning algorithm and/or a machine learning program, as described in further detail below. In the exemplary embodiment, the machine learning algorithm and/or program may be trained to identify needs and/or abnormal conditions of the user. The machine learning algorithm and/or program may further "learn" from the user data and predict needs and/or abnormal conditions associated with the user before the need and/or the abnormal condition arise.

In analyzing the received user and registration data, the MMM server may discover patterns in the user's routine. The MMM server may determine that the user picks up a maintenance medication around a certain day of every month, and the MMM server may determine this from notifications (e.g., a text message) from the pharmacy on the certain day and/or a GPS location of the user on the certain day. Accordingly, the MMM server may determine that picking up the medication from the pharmacy around the certain day every month is a pattern in the routine of the user, and the MMM server may store this discovered pattern in memory associated with the MMM server.

In analyzing the received user and registration data, the MMM server may further discover pattern disruptions in the user's routine. For example, in reference to the above, the MMM server may receive user data including multiple notifications from the pharmacy that the user needs to pick up their medication, and the MMM server may determine that the user forgot to pick up their medication around the certain day this month. Accordingly, the MMM server may determine that the user forgetting to pick up their medication was a pattern disruption. If the MMM server recognizes multiple pattern disruptions in the user's routine, the MMM server may determine, for example, that a need of the user, in addition to their medicine, is to see a doctor to have the memory of the user evaluated.

Further, for example, the MMM server may receive and store vehicle telematics data associated with the user as user data. The MMM server may determine that the user has a pattern of being a good driver because of their generally slow acceleration and braking speeds. If the MMM server receives vehicle telematics data that the braking speeds of the driver are becoming faster and faster, the MMM server may determine that there is a pattern disruption and/or abnormal condition in the driving behavior of the user. From the determined pattern disruption in the user's driving patterns, the MMM server may determine a need of the user (e.g., that the user needs to get their eyesight checked and/or that the user needs to have another driving test).

Exemplary Match Making and Provider Arrangements

In the exemplary embodiment, the MMM server may match the user to a provider based upon the determined need of the user. Providers may be, for example, caregivers (e.g., family members, friends, healthcare professionals) and third parties that provide a service (e.g., ride-sharing services, pharmacy delivery services, medical services, etc.). In the exemplary embodiment, one or more caregivers may be associated with the user.

The caregivers may be able to access the MMM application (e.g., on a mobile device associated with the caregivers), and the caregivers may be able to access the determined needs and/or abnormal conditions of the user through the MMM application and information related to the user from the MMM server. Further, the caregivers may be able to provide the MMM server with the schedule of the caregivers (e.g., work and activity schedules) and tasks that the caregivers carry out for the user (e.g., one caregiver typically picks up the user to go to an aerobics class on Monday evenings, a second caregiver typically picks up a prescription for the user in the first week of each month, and/or a third caregiver typically takes the user to their doctor's appointments when the third caregiver is not working). Further, the caregiver may allow the MMM server to access their location data (e.g., through a GPS sensor of a mobile device associated with the caregiver).

The information provided by the caregivers may allow the MMM server to determine which caregiver, if any, is available to take care of a need of the user and/or remedy an abnormal condition of the user when the MMM server determines the need and/or abnormal condition. Accordingly, the MMM server may match the user with the caregiver that satisfies scheduling criteria input by the caregivers when a need and/or abnormal condition is determined by the MMM server. Further, the MMM server may match the user with the caregiver who is in closest proximity to the location of the user, for example, if the MMM server determines a more urgent need and/or abnormal condition of the user.

Further, in the exemplary embodiment, the MMM server may match the user with a third party that provides a service based upon the determined need and/or abnormal condition of the user. For example, the third party services may be used if the MMM server determines that no caregivers are available to take care of the need and/or abnormal condition of the user. Further, for example, the caregivers may input (e.g., into the MMM application) that the caregivers prefer that the MMM server matches the user with third party services to take care of the need and/or abnormal condition of the user before the MMM server matches the user with the caregiver to take care of the need and/or abnormal condition of the user. Accordingly, the MMM server efficiently matches the user to the provider that satisfies user- and/or caregiver-specified criteria in order of preference of the user and/or caregiver to take care of the need and/or abnormal condition of the user.

After the MMM server matches the user with the provider to take care of the need and/or abnormal condition of the user, the MMM server may further automatically make arrangements with the provider on behalf of the user. For example, if the user needs to pick up a prescription at a certain time on a certain date, the MMM server may determine that none of the caregivers are available at the certain time and date, and the MMM server may then schedule a ride (e.g., through UBER or LYFT ride sharing services) for the user to the pharmacy at the certain time and date. Once the third party receives the arrangement, the third party may send a confirmation (e.g., through an application associated with the third party and/or through the MMM application) to the MMM server that the need of the user will be taken care of by the third party. Further, if the MMM server makes an arrangement with a caregiver, the caregiver may also send a confirmation (e.g., through MMM application) to the MMM server that the caregiver will take care of the determined need of the user.

Once the MMM server receives the confirmation of the generated arrangements from the providers, the MMM server may send a notification to the user notifying the user of the confirmed arrangement. The notification to the user may include, for example, a text message, a push notification, an email, a phone call, and/or any other suitable notification method.

In the exemplary embodiment, the MMM server may be configured to receive feedback from the user concerning the generated arrangements. The user may, through the MMM application, rate the arrangements and/or the provider and provide comments or feedback about the arrangements and/or the provider. Further, the MMM server may use the user feedback in making further arrangements with third parties for the user in the future. For example, if the arranged third party service was on time and friendly, the user may provide that feedback to the MMM server and rate the third party service with five stars. Further, if the MMM server determines that the user needs a third party provider again, the MMM server may request the same third party for the determined need based upon the good user feedback.

Exemplary Multi-Sided Caregiver Platform Functionality

In one aspect, the present embodiments enable senior patients, family, and professional caregivers to coordinate interaction and care, keep track of health progress and health activity, store health information and other important documents, access educational information, manage transportation, and navigate various community resources. A multi-sided caregiver platform ("MSCP") for seniors may include and/or utilize a portal and mobile application may facilitate multiple caregivers to engage third parties, such as plumbers, repairmen, doctors, or other service providers. In some embodiments, the MSCP is substantially similar to, and works in substantially the same way as MMM server, described above. In one embodiment, multiple seniors or other consumers may engage multiple service providers for services and/or products. In other embodiments, several seniors or customers may engage a single provider, or vice-versa. In other words, more than a one-to-one customer/service provider interaction(s) may be facilitated by the MSCP.

The present embodiments may use artificial intelligence and/or machine learning techniques on data, such as the data and types of data discussed elsewhere herein (such as mobile device data, mobile device sensor data, smart or interconnected home data, smart or interconnected home sensor data, smart vehicle data, smart vehicle sensor data, vehicle telematics data (such as vehicle location, speed, acceleration, cornering, deceleration, and braking data), home telematics data (such as electricity and water usage data, and occupancy and movement data), and/or other types of sensor data, including digital or other image data) to identify unmet needs of seniors or other customers, and then identify service providers to satisfy those needs. In one embodiment, the data and types of data, including sensor data, may be transformed into consumable data, or data that is otherwise digestible, for machine learning algorithms.

The present embodiments may also identify and/or schedule individual transactions and allow for electronic or other payment from a senior or other customer to a service provider. Each individual transaction may be identified and/or associated with a smart contract, and each individual transaction and/or smart contract may be placed or stored in a blockchain that may be dedicated to the customer and/or service provider, or both, as described below.

In one embodiment, whether a senior or other customer is taking prescribed medication on time and/or as prescribed may monitored. Machine learning algorithms or other artificial intelligence may identify a pattern of forgetfulness or identify the onset of forgetfulness, and if so, an electronic notification may be generated and transmitted to a mobile device of a family member or other caregiver. Machine learning may also identify when prescriptions need to be refilled, and if so, an electronic notification may be sent to a pharmacy and/or family member or other caregiver.

In some embodiments, active and/or passive monitoring of a senior may be utilized. For instance, smart home sensors and/or other sensors mounted about a home may employ active and/or passive monitoring within a home. Machine learning algorithms or other artificial intelligence may be utilized on the active and/or passive monitoring sensor data to determine irregular patterns, and if so, generate electronic notifications for family members and other caregivers.

Exemplary Smart Contracts and Blockchain

A blockchain is a distributed database that maintains a continuously-growing list of ordered records, known as blocks. Each block may contain at least a timestamp and a link to the previous block in the chain. The link to the previous block may be a hash of the previous block. For example, in the case of a service contract, the first block may contain the initial contract between a user and a service provider. The second block may contain a modification to the contract that was requested by the service provider and approved by the user. The second block may contain a hashed copy of the first block as well. The third block may contain one or more additional terms for the service contract and a hashed copy of the second block. This continues on with each block adding on to the next while containing a hash of the previous blocks in the blockchain.

To ensure the security of the information contained in the blockchain, copies of the blockchain may be distributed across multiple computer devices, known as nodes. These nodes maintain the blockchain, update the blockchain when changes occur, and ensure the stability of the blockchain itself. In some embodiments, nodes may also be used to calculate the hash of the previous blocks. As the blockchain grows, the processing power needed to calculate the hash of the previous blocks grows as well. In these embodiments, the processing of the hash may be distributed over multiple computer devices to improve the speed of processing and/or to not overburden the hashing processor. When a node processes (hashes) a block, that node is known as a miner, where the action of validating and hashing the block is also known as mining.

Accordingly, in the exemplary embodiment, once the user and the caregiver and/or service provider are matched, the MMM server or MSCP server may generate a smart contract. The smart contract may include at least one of details of the match (also called the "transaction" herein), any restrictions on the transaction, details of any insurance policies covering the parties of the transaction, and payment, such as payment card and/or checking account information. In the exemplary embodiment, the smart contract may be stored in a blockchain ledger that is distributed among a plurality of participants (also known as nodes). The nodes may be capable of communicating with the MMM server. Each match may cause the MMM server to generate a new smart contract, and each smart contract may be stored in its own blockchain ledger. As the smart contract is modified or additional information is added to the smart contract, such as completion of the transaction, another block may be added to the blockchain of the smart contract. Further, in some embodiments, each transaction between users and providers may cause the MSCP to generate a smart contract, and each transaction and/or smart contract may be stored on the blockchain.

Care Support Dashboard

In one aspect, the MSCP computer system and/or MMM computer system may include a care support dashboard for the senior and/or caregivers. The care support dashboard may graphically or through text represent various types of information about the senior. For instance, the dashboard may provide a graphical representation of the senior's gait over time. The senior's gait may be determined, for instance, by analysis of home sensor (image) data, wearable sensor data, and/or mobile device data.

The care support dashboard may also graphically represent sleep patterns as determined from sensor and/or image data. For instance, REM sleep, deep sleep, light sleep, and/or interrupted sleep patterns may be visually depicted on the dashboard.

The care support dashboard may also graphically depict a breakdown of the senior's activities, such as eating, bathing, exercise, movement, travel, socializing, appointments, etc. The care support dashboard may include an image of the senior and depict their physical conditions, such as heart rate. The care support dashboard may also include a display of upcoming activities or appointments. The dashboard may display other types of information, including those discussed elsewhere herein.

Exemplary Process for Match Making

FIG. 1 illustrates a flow chart of an exemplary computer-implemented process 100 for matching a user with a provider based upon one or more determined needs and/or abnormal conditions of a user 102. In the exemplary embodiment, user 102 may register for a multi-sided match making service (e.g., provided by a multi-sided match making server 110) through a user interface (not specifically shown) of a mobile device 106 associated with user 102, which may enable communication with a communications module 112 of multi-sided match making ("MMM") server 110. Registration data 101 for user 102 may be transmitted to MMM server 110 and may include personal information (e.g., birthday, age, height, etc.), health information (e.g., health history, current health status, etc.), and other information relating to user 102 (e.g., user's primary care doctor, ability to drive, preferred pharmacy, etc.). Registration data 101 may be stored in memory 114 of MMM server 110. In the exemplary embodiment, process 100 may be associated with matching elderly (also called "senior" herein) and/or dependent users 102 with one or more providers.

In the exemplary embodiment, once user 102 is registered for the multi-sided match making service, user 102 may be actively or passively monitored. User 102 may be monitored by sensors 104 and/or a mobile device 106 associated with user 102. Sensors 104 may include smart home devices and wearable devices. In other embodiments, sensors 104 may also include smart building sensors, aerial device sensors, smart vehicle sensors, autonomous or semi-autonomous vehicle sensors, and/or other sensors. When user 102 carries out an action 103, sensors 104 and/or mobile device 106 may detect action 103. For example, if user 102 asks their smart home device a question, sensor 104 detects this action 103 (e.g., the asking of the question). Further, for example, if user 102 makes an appointment on mobile device 106 through an application, mobile device 106 detects this action 103 (e.g., the making of the appointment).

In response to detecting action 103, sensors 104 and/or mobile device 106 may generate user data 108 related to action 103 and may transmit generated user data 108 to MMM server 110. In the exemplary embodiment, user data 108 may be transmitted to MMM server 110 from sensors 104 and/or mobile device 106. In some embodiments, MMM server 110 may be associated with sensors 104 and/or mobile device 106 and may actively retrieve user data 108 from memory 114 of MMM server 110.

In the exemplary embodiment, user data 108 may be retrieved and stored in memory 114 of MMM server 110. MMM server 110 may analyze user data 108 and generate a determined need 118 based upon analyzed user data 108. In some embodiments, determined need 118 also includes a determined abnormal condition of user 102. For example, if user data 108 is related to user 102 making a doctor's appointment, and MMM server 110 retrieves (e.g., from registration data 101 in memory 114) that user 102 cannot drive, MMM server may determine that user 102 needs a ride to the scheduled doctor's appointment. MMM server 110 may transmit determined need 118 to a mobile device 122 (e.g., through a notification to mobile device 122 and/or through a multi-sided match making application on mobile device 122) associated with a caregiver 120 of user 102. Further, MMM server 110 may transmit determined need 118 to a third party server 124 associated with a third party in order to match user 102 with the third party. Third party server 124 may be a server associated with a provider and/or service (e.g., ride-sharing service server, taxi, doctor server, housecleaning service server, drycleaner, restaurant, grocery store, utilities, plumber, pharmacy, etc.).

In the exemplary embodiment, caregiver 120 may input registration data (e.g., scheduling/calendar data and task data) into and allow MMM server 110 to access location data relating to caregiver 120, and registration and location data 123 associated with caregiver 120 may be transmitted to MMM server 110 from caregiver 120 (e.g., through mobile device 122 of caregiver 120).

MMM server 110 may further generate arrangements with at least one of caregiver 120 and third party server 124 based upon determined need 118 of user 102 and availability and/or location (relative to a location of user 102) of caregiver 120 (e.g., determined from registration and location data 123 of caregiver 120). For example, if caregiver 120 typically takes user 102 to doctor's appointments, MMM server 110 may generate arrangements with caregiver 120 when user 102 schedules a doctor's appointment. Further, for example, caregiver 120 may indicate to MMM server 110 (e.g., through registration and location data 123) that caregiver 120 is unavailable on weekdays.

Accordingly, if user 102 makes a doctor's appointment on a weekday, MMM server 110 may generate arrangements with a third party (e.g. a ride-sharing service) via third party server 124 for the third party to take user 102 to doctor's appointment. If the arrangements generated by MMM server 110 with caregiver 120 work for caregiver 120, caregiver 120 may send (e.g., via mobile device 122) a confirmation 127 to MMM server 110. Further, if arrangements generated by MMM server 110 with third party server 124 work for the third party, third party server 124 may send a confirmation 126 to MMM server 110. MMM server 110 may transmit a notification 128 to user 102 including determined need 118 and confirmation 126, 127 from third party server 124 and/or caregiver 120 that determined need 118 will be met by the third party and/or caregiver 120. Further, once generated arrangements are confirmed with caregiver 120 and/or third party server 124 (e.g., through confirmations 126 and/or 127), MMM server may further generate a smart contract (not specifically shown) between user 102 and caregiver 120 and/or the third party, and MMM server may store the generated smart contract on a blockchain (not shown).

In the current embodiment, one caregiver 120 and one third party server 124 are shown for ease of illustration. However, MMM server 110 may transmit determined need 118 to, and make arrangements with, multiple caregivers 120 and/or multiple third party servers 124.

Third party server 124, mobile device 122 of caregiver 120, and/or the blockchain may be capable of communicating with MMM server 110 though an application programming interface (API) 116. In the exemplary embodiment, MMM server 110 may include a firewall (not shown) to protect the private and/or personally identifiable information of user 102. As determined needs 118 and/or arrangements are modified or additional information is received and transmitted, more data may be added to the databases of memory 114 and/or to the blockchain via smart contracts.

In accordance with an exemplary embodiment of MMM server 110, for example, user 102 may be notified on mobile device 106 that user 102 has forgotten to pick up their prescription from a pharmacy for a third time this week. Upon receiving this notification, mobile device 106 may generate user data 108 associated with the notification and transmit generated user data 108 to MMM server 110. From user data 108 and registration data 101, MMM server 110 may determine that a need 118 of user 102 is their prescription and may generate an arrangement to remind user 102 to pick up their prescription or arrange for the prescription to be delivered to user 102. MMM server 110 may communicate with third party server 124 (e.g., associated with the pharmacy of user 102) and determine that the pharmacy offers prescription delivery.

Accordingly, MMM server 110 may arrange the prescription delivery with third party server 124 and receive a delivery confirmation 126 from third party server 124. MMM server 110 may then send notification 128 to user 102 via mobile device 106 (or any other suitable device associated with user 102) notifying user 102 that their prescription will be delivered. Further, MMM server 110 may notify caregiver 120 of user 102 that user 102 had not picked up their prescription from the pharmacy for the third time that week and that MMM server 110 has arranged for the pharmacy to deliver the prescription to user 102. MMM server 110 may prompt caregiver 120 to determine if caregiver 120 wants MMM server 110 to set up an appointment for an evaluation of user 102 with a doctor (via third party server 124) since user 102 forgot to pick up their prescription three times. For example, based upon registration data 101 (e.g., age) and user data 108 (e.g., forgetting prescription), MMM server 110 may determine that user 102 is at risk for dementia and should be further evaluated. Computer-implemented process 100 may include additional, less, or alternate actions, including those discussed elsewhere herein.

Exemplary Multi-Sided Match Making System

Figure 2:
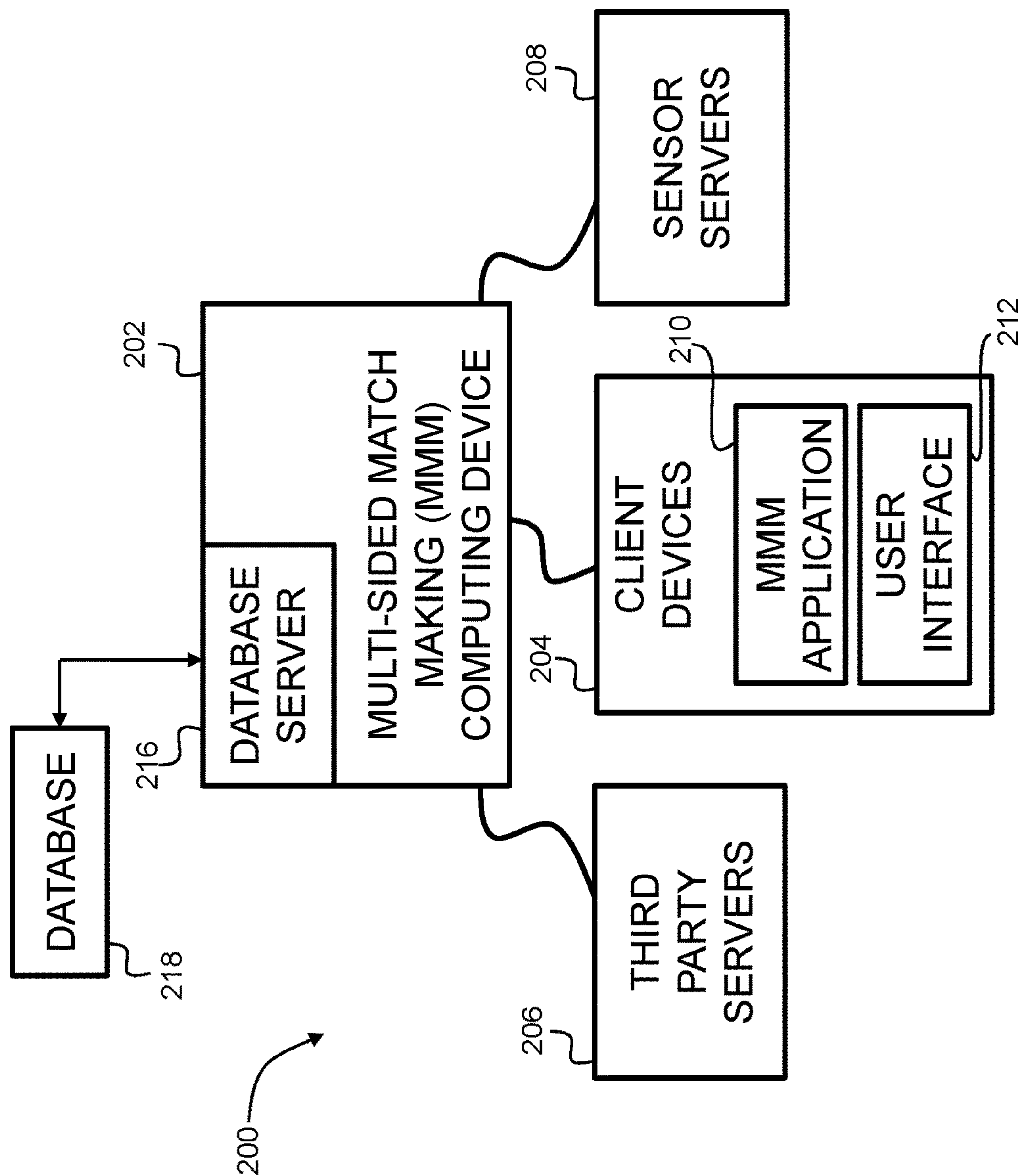
FIG. 2 illustrates an exemplary multi-sided match making computer system for electronically matching users to providers in accordance with the present disclosure.

FIG. 2 depicts a view of an exemplary multi-sided match making ("MMM") system 200 that may be used in implementing process 100 shown in FIG. 1. In the exemplary embodiment, MMM system 200 may be used in matching a user with a provider based upon one or more determined needs of the user. MMM system 200 may include a multi-sided match making ("MMM") computing device 202. In some embodiments MMM computing device 202 is similar to MMM server 110 (shown in FIG. 1).

In the exemplary embodiment, MMM computing device 202 is in communication with client devices 204, third party servers 206, and sensor servers 208. MMM computing device 202 is also in communication with database 218 and may communicate with a database 218 through a database server 216. In some embodiments, database server 216 is a component of MMM computing device 202. In other embodiments, database server 216 is separate from MMM computing device 202. In some embodiments, MMM system 200 may include a plurality of MMM computing devices 202, client devices 204, third party servers 206, sensor servers 208, and/or databases 218.

In the exemplary embodiment, client devices 204 may be computers that include a web browser or a software application, which enables client devices 204 to access remote computer devices, such as MMM computing device 202, using the Internet or other network. More specifically, client devices 204 may be communicatively coupled to the Internet through many interfaces including, but not limited to, at least one of a network, such as the Internet, a local area network (LAN), a wide area network (WAN), or an integrated services digital network (ISDN), a dial-up-connection, a digital subscriber line (DSL), a cellular phone connection, and a cable modem. Client devices 204 may be any device capable of accessing the Internet including, but not limited to, a desktop computer, a laptop computer, a personal digital assistant (PDA), a cellular phone, a smartphone, a tablet, a phablet, wearable electronics, smart watch, or other web-based connectable equipment or mobile devices. Further, MMM computing device 202 may be communicatively coupled to client devices 204 and may receive information from client devices 204.

In the exemplary embodiment, MMM computing device 202 may interact with third party servers 206 associated with third parties that provide a service (e.g., UBER, LYFT, CVS, WALGREENS, etc.). For example, MMM computing device 202 may communicate with an application associated with third party servers 206 to arrange services for user 102 (shown in FIG. 1). MMM computing device 202 and third party servers 206 may be communicatively coupled to one another through the Internet through many interfaces including, but not limited to, at least one of a network, such as the Internet, a local area network (LAN), a wide area network (WAN), or an integrated services digital network (ISDN), a dial-up-connection, a digital subscriber line (DSL), a cellular phone connection, and a cable modem.

In the exemplary embodiment, MMM computing device 202 may receive data from sensor servers 208 and may use the data to generate user data 108 (as shown in FIG. 1). For example, MMM computing device 202 may receive user data 108 generated by sensor servers 208 based upon actions 103 (shown in FIG. 1) carried out by user 102. Sensor servers 208 may include smart home device servers (e.g., AMAZON and GOOGLE servers) and wearable device servers (e.g., FITBIT AND APPLE servers). User data 108 may include interaction data from a smart home device (e.g., AMAZON ALEXA and GOOGLE HOME) and activity and/or location data from a wearable device (e.g., FITBIT and APPLE WATCH) and/or autonomous or semi-autonomous vehicles (and/or smart vehicle sensors). MMM computing device 202 and sensor servers 208 may be communicatively coupled through any suitable connection including through the Internet through many interfaces including, but not limited to, at least one of a network, such as the Internet, a local area network (LAN), a wide area network (WAN), or an integrated services digital network (ISDN), a dial-up-connection, a digital subscriber line (DSL), a cellular phone connection, and a cable modem.

Database server 216 may be communicatively coupled to database 218 that stores data. In one embodiment, database 218 may include registration data 101 (shown in FIG. 1), user data 108 (shown in FIG. 1), sensor data, mobile device data, confirmation data, and notification data. In the exemplary embodiment, database 218 may be stored remotely from MMM computing device 202. In some embodiments, database 218 may be decentralized. In the exemplary embodiment, a user, such as user 102 or caregiver 120 (shown in FIG. 1), may access database 218 via their respective client devices 204 by logging onto MMM computing device 202, as described herein.

In the exemplary embodiment, client devices 204 include a multi-sided match making ("MMM") application 210 and a user interface 212. User interface 212 may be used, for example, to receive notifications from MMM computing device 202 and/or to input and verify information to be sent to MMM computing device 202. MMM application 210 may be, for example, a program or application that runs on client device 204.

In some embodiments, MMM application 210 is accessed remotely by client device 204. MMM application 210 may be hosted by or stored on MMM computing device 202 and accessed by client device 204. For example, MMM application 210 may be stored on and executed by MMM computing device 202. Client device 204 may provide inputs to MMM computing device 202 via a network which are used by MMM computing device 202 to execute MMM application 210. In one embodiment, these inputs may be received by a website hosted by MMM computing device 202. The website may further provide output to client device 204. Client device 204 used by the user (e.g., user 102 and/or caregiver 120) has access to a website (e.g., hosted by MMM computing device 202), application (e.g., MMM application 210), or other tool which the user uses to receive and/or view determined needs 118 (shown in FIG. 1), third party confirmation 126 (shown in FIG. 1), caregiver confirmations 127 (shown in FIG. 1), notifications 128 (shown in FIG. 1), and analyzed user data 108 (shown in FIG. 1), provided by MMM computing device 202 to the user. MMM system may be configured with additional, less, or alternate functionality, including that discussed elsewhere herein.

Exemplary User Computer Device

Figure 3:
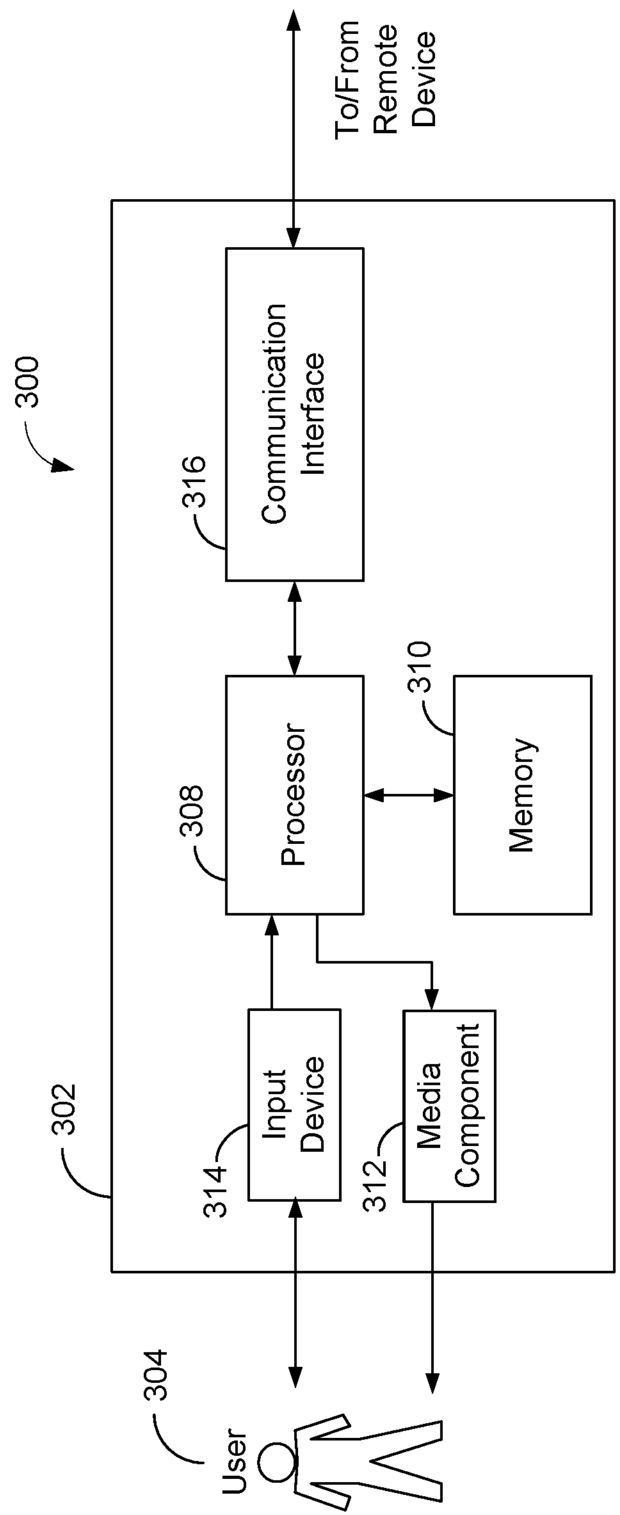
FIG. 3 illustrates an exemplary configuration of an exemplary user computing device that may be used in the multi-sided match making computer system illustrated in FIG. 2.

FIG. 3 illustrates an exemplary configuration 300 of an exemplary user computing device 302. In some embodiments, user computing device 302 may be in communication with a multi-sided match making computing device (such as MMM server 110, shown in FIG. 1 or MMM computing device 202, shown in FIG. 2). User computing device 302 may be representative of, but is not limited to client devices 204, third party servers 206, and/or sensor servers 208. For example, user computing device 302 may be a mobile device, smartphone, tablet, smartwatch, wearable electronic, laptop, desktop, or another type of computing device associated with an account holder (e.g., user 102 and/or caregiver 120).

User computer device 302 may be operated by a user 304 (e.g., a user of MMM system 200, shown in FIG. 2 and substantially similar to user 102 and caregiver 120, shown in FIG. 1). User computer device 302 may receive input from user 304 via an input device 314. User computer device 302 includes a processor 308 for executing instructions. In some embodiments, executable instructions may be stored in a memory area 310. Processor 308 may include one or more processing units (e.g., in a multi-core configuration), and processor 308 may include, be in communication with, and/or be associated with one or more transceivers (not specifically shown). Memory area 310 may be any device allowing information such as executable instructions and/or user and registration data to be stored and retrieved. Memory area 310 may include one or more computer-readable media.

User computer device 302 also may include at least one media output component 312 for presenting information to user 304. Media output component 312 may be any component capable of conveying information to user 304 and may be used to at least partially implement user interface 212 (shown in FIG. 2). In some embodiments, media output component 312 may include an output adapter (not shown), such as a video adapter and/or an audio adapter. An output adapter may be operatively coupled to processor 308 and operatively coupleable to an output device, such as a display device (e.g., a cathode ray tube (CRT), liquid crystal display (LCD), light emitting diode (LED) display, or "electronic ink" display) or an audio output device (e.g., a speaker or headphones).

In some embodiments, media output component 312 may be configured to present a graphical user interface (e.g., a web browser and/or a client application) to user 304. A graphical user interface may include, for example, calendars for user 102 and/or caregiver 120, notifications for user 102, determined needs 118 of user 102, and/or an activity profile of user 102.

In some embodiments, user computer device 302 may include input device 314 for receiving input from user 304. User 304 may use input device 314 to, without limitation, interact with MMM system 200 (e.g., using MMM application 210), MMM computing device 202, or any of client devices 204, third party servers 206, and sensor servers 208 (shown in FIG. 2). Input device 314 may include, for example, a keyboard, a pointing device, a mouse, a stylus, and/or a touch sensitive panel (e.g., a touch pad or a touch screen) and may be used to at least partially implement user interface 212 (shown in FIG. 2). A single component, such as a touch screen, may function as both an output device of media output component 312 and input device 314. User computer device 302 may further include at least one sensor, including, for example, a gyroscope, an accelerometer, a position detector, a biometric input device, and/or an audio input device. In some embodiments, at least some data collected by user computer device 302 may be transmitted to MMM computing device 202. In the exemplary embodiment, data collected by user computer device 302 may be included in user data 108.

User computer device 302 may also include a communication interface 316, communicatively coupled to any of MMM computing device 202, client devices 204, third party servers 206, and sensor servers 208. Communication interface 316 may include, for example, a wired or wireless network adapter and/or a wireless data transceiver for use with a mobile telecommunications network.

Stored in memory area 310 may be, for example, computer-readable instructions for providing a user interface to user 304 via media output component 312 and, optionally, receiving and processing input from input device 314. The user interface may include, among other possibilities, a web browser and/or a client application. Web browsers enable users, such as user 304, to display and interact with media and other information typically embedded on a web page or a website hosted by MMM computing device 202 and/or client device 204. A client application may allow user 304 to interact with, for example, any of MMM computing device 202, client devices 204, third party servers 206, and sensor servers 208. For example, instructions may be stored by a cloud service and the output of the execution of the instructions sent to the media output component 312. User computing device 302 may include additional, less, or alternate functionality, including that discussed elsewhere herein.

Exemplary Server Device

Figure 4:
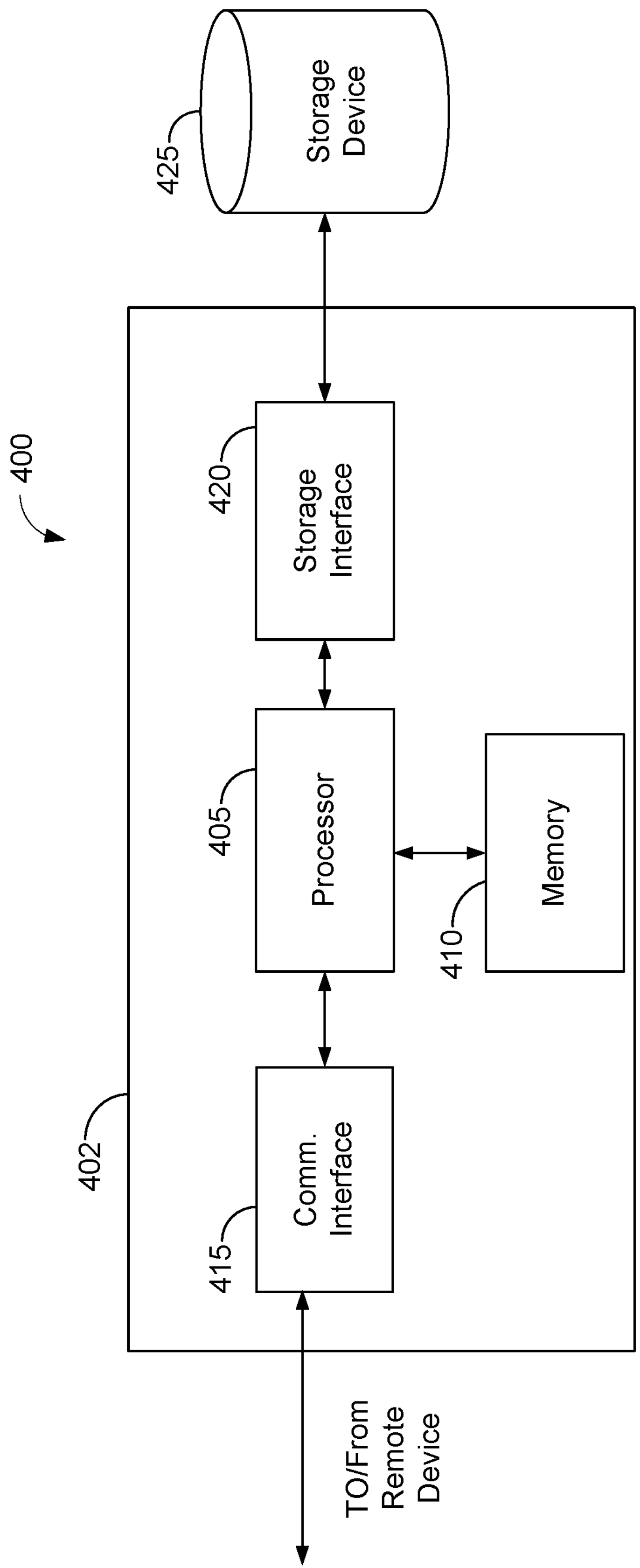
FIG. 4 illustrates an exemplary configuration of an exemplary server computing device that may be used in the multi-sided match making computer system illustrated in FIG. 2.

FIG. 4 depicts an exemplary configuration 400 of an exemplary server computing device 402, in accordance with one embodiment of the present disclosure. Server computer device 402 may include, but is not limited to, MMM computing device 202 (shown in FIG. 2). Server computer device 402 may include a processor 405 for executing instructions. Instructions may be stored in a memory area 410. Processor 405 may include one or more processing units (e.g., in a multi-core configuration), and processor 405 may include, be in communication with, and/or be associated with one or more transceivers (not specifically shown).

Processor 405 may be operatively coupled to a communication interface 415 such that server computer device 402 may be capable of communicating with a remote device such as another server computer device 402 or a user computing device, such as client device 204 (shown in FIG. 2). For example, communication interface 415 may receive requests from or transmit requests to client devices 204 via the Internet.

Processor 405 may also be operatively coupled to a storage device 425. Storage device 425 may be any computer-operated hardware suitable for storing and/or retrieving data, such as, but not limited to, data associated with database 218 (shown in FIG. 2). In some embodiments, storage device 425 may be integrated in server computer device 402. For example, server computer device 402 may include one or more hard disk drives as storage device 425. In other embodiments, storage device 425 may be external to server computer device 402 and may be accessed by a plurality of server computer devices 402. For example, storage device 425 may include a storage area network (SAN), a network attached storage (NAS) system, and/or multiple storage units such as hard disks and/or solid state disks in a redundant array of inexpensive disks (RAID) configuration.

In some embodiments, processor 405 may be operatively coupled to storage device 425 via a storage interface 420. Storage interface 420 may be any component capable of providing processor 405 with access to storage device 425. Storage interface 420 may include, for example, an Advanced Technology Attachment (ATA) adapter, a Serial ATA (SATA) adapter, a Small Computer System Interface (SCSI) adapter, a RAID controller, a SAN adapter, a network adapter, and/or any component providing processor 405 with access to storage device 425.

Processor 405 executes computer-executable instructions for implementing aspects of the disclosure. In some embodiments, processor 405 may be transformed into a special purpose microprocessor by executing computer-executable instructions or by otherwise being programmed.

Exemplary Computer-Implemented Method

Figure 5:
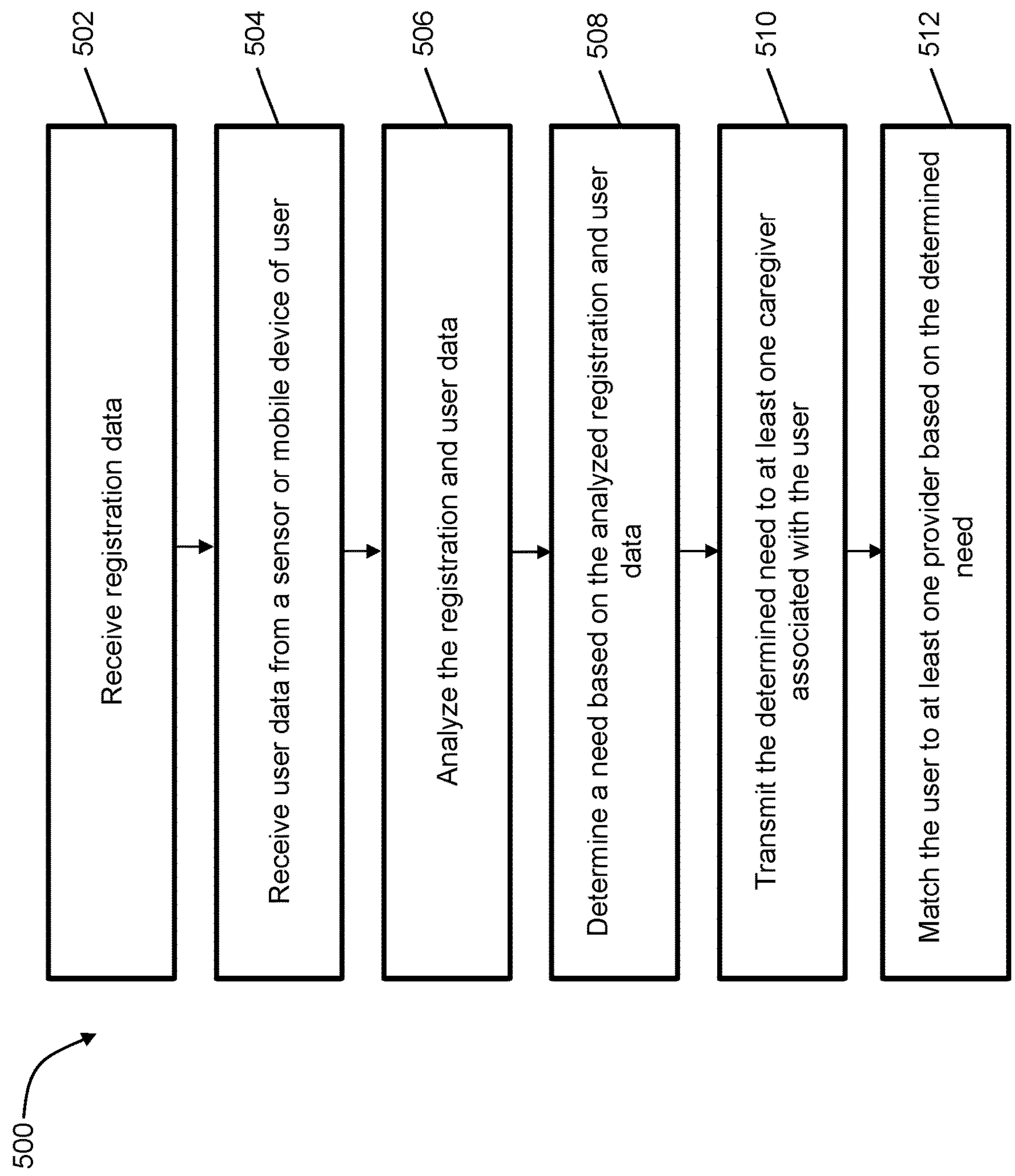
FIG. 5 illustrates a flow chart of an exemplary computer-implemented method implemented by the exemplary multi-sided match making computer system shown in FIG. 2.

FIG. 5 depicts a flow chart illustrating a computer-implemented method 500 for matching users to providers based upon a determined need. In the exemplary embodiment, method 500 may be implemented by a multi-sided match making computer system such as MMM server 110 (shown in FIG. 1) and MMM computing device 202 (shown in FIG. 2).

Method 500 may include receiving 502 registration data from a user (e.g., user 102 shown in FIG. 1). Method 500 may also include receiving 504 user data (e.g., user data 108 shown in FIG. 1) from at least one of a sensor (e.g., sensors 104 shown in FIG. 1) or mobile device (e.g., mobile device 106 shown in FIG. 1) of the user. The user data may be generated in response to an action carried out by the user.

Method 500 may further include analyzing 506 the received 502, 504 registration and user data and determining 508 a need (e.g., determined need 118 shown in FIG. 1) of the user based upon the analyzed 506 registration and user data. Method 500 may include transmitting 510 the determined need to at least one caregiver (e.g., caregivers 120 shown in FIG. 1) associated with the user. Method 500 may additionally include matching 512 the user to at least one provider (e.g., a third party associated with third party server 124 and/or caregiver 120 shown in FIG. 1) based upon the determined 508 need. Matching 512 may occur between the user and the provider because the provider may offer to take care of the determined 508 need. Method 500 may include additional, less, or alternate actions, including those discussed elsewhere herein.

Exemplary Computer Device

Figure 6:
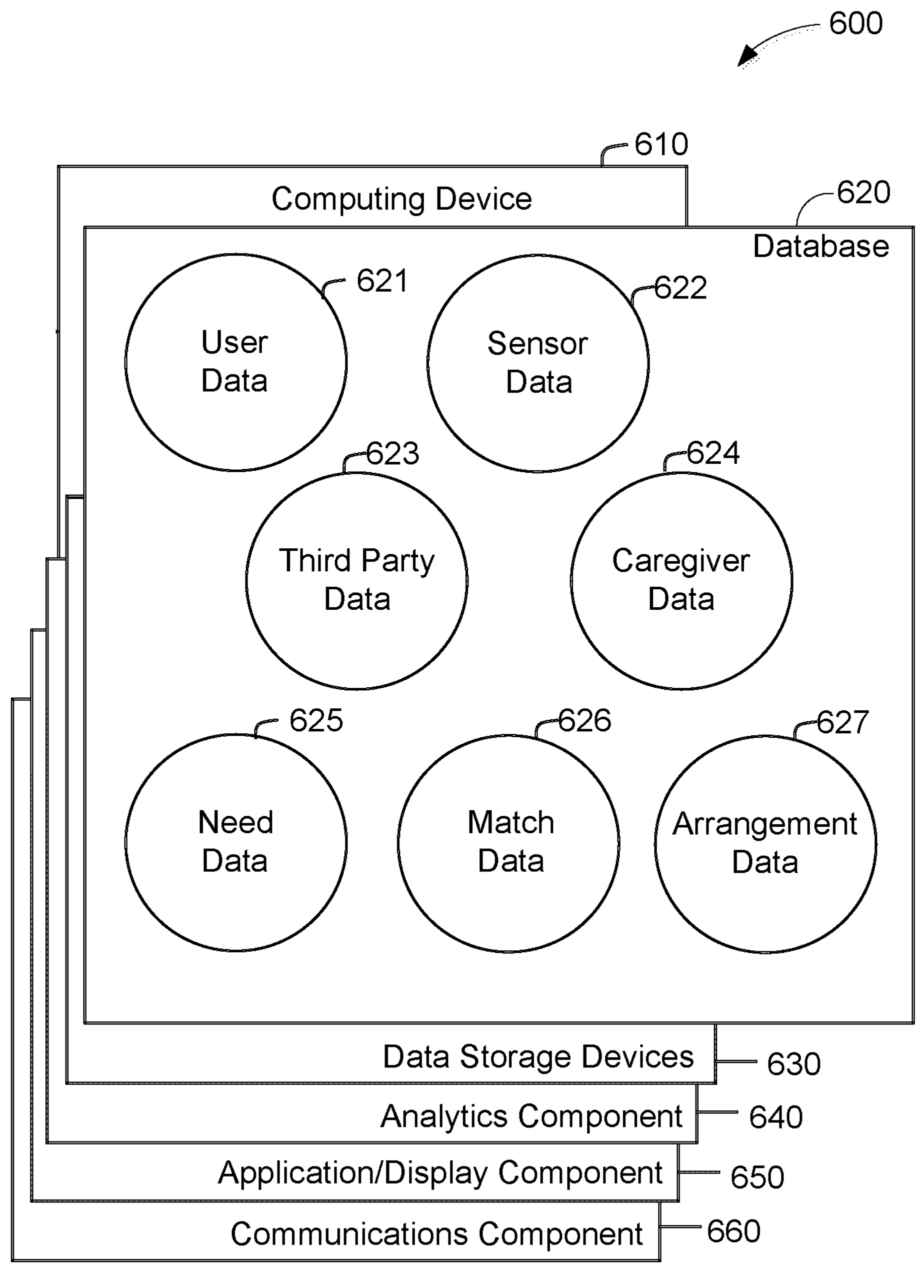
FIG. 6 illustrates a diagram of components of one or more exemplary computing devices that may be used in the multi-sided match making computer system shown in FIG. 2.

FIG. 6 depicts a diagram 600 of components of one or more exemplary computing devices 610 that may be used in multi-sided match making system 200 (shown in FIG. 2). In some embodiments, computing device 610 may be similar to MMM server 110 (shown in FIG. 1) and MMM computing device 202 (shown in FIG. 2). Database 620 may be coupled with several separate components within computing device 610, which perform specific tasks. In this embodiment, database 620 may include user data 621, sensor data 622, third party data 623, caregiver data 624, need data 625, match data 626, and arrangement data 627. In some embodiments, database 620 is similar to database 218 (shown in FIG. 2). In further embodiments, match data 626 and/or arrangement data 627 may be stored as smart contracts on a blockchain that is in communication with database 620.

Computing device 610 may include database 620, as well as data storage devices 630. Computing device 610 may also include an analytics component 640 for analyzing registration data 101 and user data 108 and determining a need 118

(all shown in FIG. 1). Computing device 610 may further include application/display component 650 for generating and displaying information to users, such as through MMM application 210 (shown in FIG. 2), and supporting MMM application 210. Moreover, computing device 610 may include communications component 660 for receiving and transmitting data, such as user data 621, sensor data 622, third party data 623, caregiver data 624, need data 625, match data 626, and arrangement data 627. Computing devices 610 may include additional, less, or alternate functionality, including that discussed elsewhere herein.

Exemplary Multi-Sided Caregiver Platform Functionality

Figure 7:
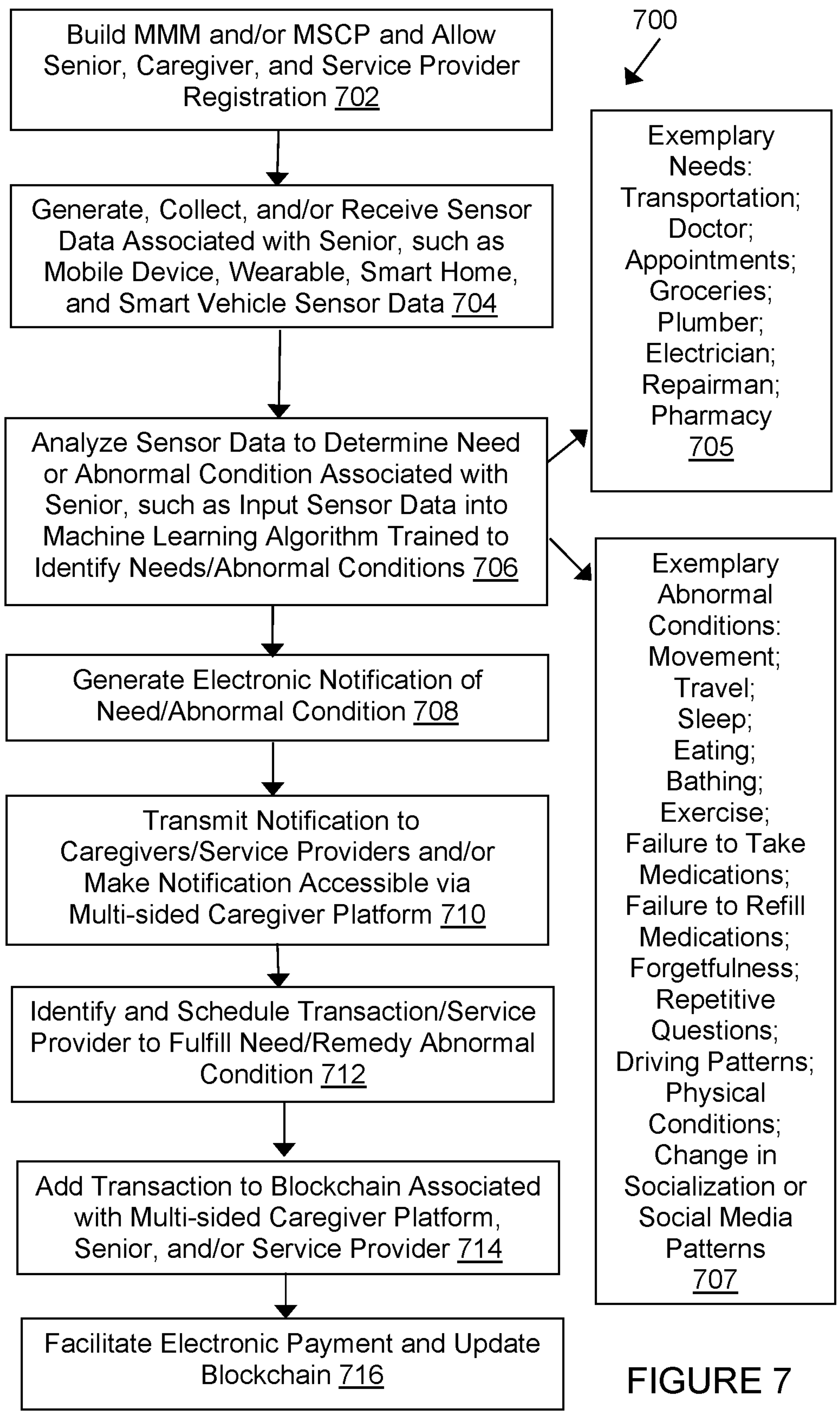
FIG. 7 illustrates an exemplary computer-implemented method associated with a multi-sided caregiver platform (MSCP) computer system as described herein.

FIG. 7 illustrates an exemplary computer-implemented method 700 associated with a multi-sided caregiver platform ("MSCP") computer system and/or multi-sided match making ("MMM") computer system, which are together referred to as "platforms." Computer-implemented method 700 may be substantially similar to process 100 (shown in FIG. 1) and/or method 500 (shown in FIG. 5). Computer-implemented method 700 may include building 702 the platforms. The platforms may be configured to allow 702 seniors, senior patients, caregivers (such as family members and professional caregivers), and service and product providers to register (e.g., with registration data 101 of user 102 and/or registration and location data 123 of caregiver 120, shown in FIG. 1) with the MMM and/or MSCP computer systems, such as build a profile and enter name, address, and preference information.

In the exemplary embodiment, computer-implemented method 700 may include, via one or more processors and/or associated transceivers, receiving, generating, and/or collecting 704 sensor data and/or mobile device data (e.g., user data 108 generated by sensors 104 and/or mobile device 106, shown in FIG. 1) associated with a senior. For instance, computer-implemented method 700 may include receiving 704, via one or more processors and/or associated transceivers and via wireless communication and/or data transmission over one or more radio frequency links, sensor and/or mobile device data (e.g., user data 108, shown in FIG. 1) associated with a user or customer, such as a senior or senior patient. The sensor and/or mobile device data may be generated and transmitted by mobile devices, smart home sensors and controllers, autonomous or semi-autonomous or smart vehicle controllers or processors, wearable devices, smart aerial devices or smart drones, smart infrastructure sensors, etc.

Computer-implemented method 700 may include, via one or more processors and/or associated transceivers, analyzing 706 the sensor data to determine or identify a developing or unmet need (e.g., determined need 118, shown in FIG. 1) of the senior, or determine or identify an abnormal condition associated with the senior. In some embodiments, the sensor data may be analyzed 706 by being input into a machine learning algorithm, model, or program trained to identify developing or unmet needs 705 of a senior, and/or determine or identify an abnormal condition 707 associated with the senior. In some embodiments, unmet needs 705 and abnormal conditions 707 may be substantially similar to determined need 118 (shown in FIG. 1).

In some embodiments, developing or unmet need 705 of the senior identified by the computer system may include a need for: transportation, a doctor, various appointments, groceries, plumbing services, electrical services, various repair work, pharmacy attention, and/or other unmet needs 705, including those discussed elsewhere herein.

In some embodiments, abnormal conditions 707 associated with the senior identified by the computer system may include abnormal, or a change in: (a) movement, travel, sleep, eating, bathing, showering, exercise, and/or socialization patterns; (b) forgetfulness; (c) physical conditions; (d) socialization, social media usage, mobile device usage, telephone usage, email or text communication; and/or (e) other behavior patterns discussed herein. Abnormal conditions 707 associated with the senior identified by the computer system may include failure to take medications; failure to refill medications; change or lapse in memory; repetitive questions or speech; and/or other conditions, including those discussed elsewhere herein.

Computer-implemented method 700 may include generating 708, via one or more processors and/or associated transceivers, an electronic notification of an identified need or abnormal condition of the senior, such as those described elsewhere herein. Computer-implemented method 700 may include, via one or more processors and/or associated transceivers, transmitting 710, via wireless communication or data transmission over one or more radio frequency links, the generated 708 electronic notification to a mobile device (e.g., mobile device 122, shown in FIG. 1), or other computing device, associated with family members and other caregivers (e.g., caregiver 120, shown in FIG. 1), and/or service providers (e.g., third parties, described with respect to FIG. 1), and otherwise make 710 the generated 708 electronic notification available to the network participants via the platforms.

Computer-implemented method 700 may include, via one or more processors and/or associated transceivers, identifying and/or scheduling 712 a transaction and/or service provider to meet unmet need 705 and/or remedy abnormal condition 707 (e.g., making arrangements with the provider, as described herein). The service provider may identified based upon social media reviews and/or proximity to the customer/senior. For instance, service providers may be selected based upon proximity to a senior's mobile device GPS (Global Positioning System) location and availability, as well as each service provider's location, proximity to the senior, and availability.

Computer-implemented method 700 may include, via one or more processors and/or associated transceivers, adding 714 each transaction to a blockchain, such as a blockchain associated with the platforms or the senior, caregiver, or service provider. Each transaction may also be also associated with a smart contract.

Computer-implemented method 700 may include, via one or more processors and/or associated transceivers, transferring 716 funds electronically from a virtual account associated with the senior to a financial account of the service provider. For instance, payment for each transaction (e.g., arrangement and/or match) may be electronic in some embodiments, and may be recorded on the blockchain.

Exemplary Embodiments

In one aspect, a multi-sided match making ("MMM") computer system for matching consumers to providers may be provided. The MMM computer system may include at least one processor in communication with at least one memory device, the at least one processor is programmed to: (1) receive registration data from a user; (2) receive user data from at least one of a sensor and a mobile device associated with the user, wherein the user data is generated by the at least one of the sensor and the mobile device in response to an action carried out by the user; (3) analyze the registration data and the user data; (4) determine a need based upon the analyzed registration and user data; (5) transmit the determined need to at least one caregiver associated with the user; and/or (6) match the user to at least one provider based upon the determined need, wherein the provider is at least one of the caregiver, another caregiver, and a service, and wherein the provider is able to meet the determined need for the user. The MMM computer system may include additional, less, or alternate functionality, including that discussed elsewhere herein.

For instance, the processor may be further programmed to: (i) automatically generate arrangements with the provider based upon the determined need of the user; (ii) transmit the generated arrangements to the provider; (iii) receive confirmation from the provider regarding the arrangements, wherein the confirmation confirms that the provider will meet the determined need of the user; and/or (iv) send a notification to the user including the confirmed arrangements.

The processor may be programmed to receive feedback from the user regarding the generated arrangements. The processor may be further programmed to store in the at least one memory device information including (i) the received user and registration data, (ii) the determined need of the user, (iii) the matching of the user and the provider for the determined need of the user, (iv) the generated arrangements, and/or (v) the feedback from the user regarding the generated arrangements.

The processor may be programmed to determine needs for the user, match the user to the provider, and generate arrangements for the user by using machine learning techniques on the stored information. The processor may be further programmed to: discover patterns of the user from the stored information; and/or recognize a pattern disruption of the user, wherein the pattern disruption is recognized when the user data demonstrates a deviation from the discovered patterns of the user.

The registration data may include at least one of an age, a birthdate, a height, a weight, a medical history, and preferred doctors and pharmacies of the user. The sensors may include mobile devices, smart home devices and wearable devices, and/or other sensors, such as autonomous or semi-autonomous vehicle sensors, or aerial device sensors. The action carried out by the user may include at least one of interacting with the smart home device of the user, autonomous or semi-autonomous vehicle of the user, scheduling an appointment on the mobile device, receiving a notification on the mobile device, conversing on the mobile device, and exercising.

In another aspect, a computer-implemented method for matching consumers to providers may be provided. The method may be implemented using a multi-sided match making ("MMM") computer system including at least one processor in communication with at least one memory device. The method may include: (1) receiving registration data from a user; (2) receiving user data from at least one of a sensor and a mobile device associated with the user, wherein the user data is generated by the at least one of the sensor and the mobile device in response to an action carried out by the user; (3) analyzing the registration data and the user data; (4) determining a need based upon the analyzed registration and user data; (5) transmitting the determined need to at least one caregiver associated with the user; and/or (6) matching the user to at least one provider based upon the determined need, wherein the provider is at least one of the caregiver, another caregiver, and a service, and wherein the provider is able to meet the determined need for the user. The method may include additional, less, or alternate functionality, including that discussed elsewhere herein.

For instance, the method may further include (i) automatically generating arrangements with the provider based upon the determined need of the user; (ii) transmitting the generated arrangements to the provider; (iii) receiving confirmation from the provider regarding the arrangements, wherein the confirmation confirms that the provider will meet the determined need of the user; and/or (iv) sending a notification to the user including the confirmed arrangements.

The method may include receiving feedback from the user regarding the generated arrangements. The method may include storing in the at least one memory device information including (i) the received user and registration data, (ii) the determined need of the user, (iii) the matching of the user and the provider for the determined need of the user, (iv) the generated arrangements, and/or (v) the feedback from the user regarding the generated arrangements.

The method may include determining needs for the user, matching the user to the provider, and generating arrangements for the user by using machine learning techniques on the stored information. The method may include: discovering patterns of the user from the stored information; and/or recognizing a pattern disruption of the user, wherein the pattern disruption is recognized when the user data demonstrates a deviation from the discovered patterns of the user.

The registration data may include at least one of an age, a birthdate, a height, a weight, a medical history, preferred doctors and pharmacies of the user, preferred transportation companies of the user, and other preferred service providers of the user. The sensors include smart home devices and wearable devices, and the action carried out by the user includes at least one of interacting with the smart home device of the user, scheduling an appointment on the mobile device, receiving a notification on the mobile device, conversing on the mobile device, and exercising. In other embodiments, the sensors may also include autonomous or semi-autonomous vehicle sensors, and/or other sensors, such as smart city sensors or aerial device sensors.

In another aspect, at least one non-transitory computer-readable media having computer-executable instructions thereon is provided. Wherein when executed by at least one processor of a multi-sided match making ("MMM") computer system, the instructions cause the at least one processor of the MMM computer system to: (1) receive registration data from a user; (2) receive user data from at least one of a sensor and a mobile device associated with the user, wherein the user data is generated by the at least one of the sensor and the mobile device in response to an action carried out by the user; (3) analyze the registration data and the user data; (4) determine a need based upon the analyzed registration and user data; (5) transmit the determined need to at least one caregiver associated with the user; and/or (6) match the user to at least one provider based upon the determined need, wherein the provider is at least one of the caregiver, another caregiver, and a service, and wherein the provider is able to meet the determined need for the user.

The instructions may further cause the at least one processor of the MMM computing device to: automatically generate arrangements with the provider based upon the determined need of the user; transmit the generated arrangements to the provider; receive confirmation from the provider regarding the arrangements, wherein the confirmation confirms that the provider will meet the determined need of the user (and/or abnormal condition associated with the user, as discussed elsewhere herein); and/or send a notification to the user including the confirmed arrangements.

The instructions may also cause the at least one processor of the MMM computing device to: receive feedback from the user regarding the generated arrangements. The instructions may further cause the at least one processor of the MMM computing device to: store in the at least one memory device information including (i) the received user and registration data, (ii) the determined need of the user, (iii) the matching of the user and the provider for the determined need of the user (and/or abnormal condition associated with the user), (iv) the generated arrangements, and/or (v) the feedback from the user regarding the generated arrangements.

The instructions may cause the at least one processor of the MMM computing device to: determine needs for the user, match the user to the provider, and generate arrangements for the user by using machine learning techniques on the stored information. The instructions may further cause the at least on processor of the MMM computing device to: discover patterns of the user from the stored information; and/or recognize a pattern disruption of the user, wherein the pattern disruption is recognized when the user data demonstrates a deviation from the discovered patterns of the user. The instructions may direct additional, less, or alternate functionality, including that discussed elsewhere herein.

Exemplary MSCP Embodiments

In one aspect, a multi-sided caregiver platform (MSCP) computer system for matching consumers to providers may be provided. The MSCP computer system may include at least one processor and associated transceiver in communication with at least one memory device. The at least one processor and/or transceiver may be programmed to: (i) allow participants to register with the MSCP, such as via wireless communication or data transmission and a dedicated website and/or mobile application, the participants including seniors, caregivers, and/or service providers; (ii) receive sensor data associated with a senior via wireless communication or data transmission from a transceiver associated with a mobile device, smart home controller, smart vehicle, or wearable device, the sensor data including mobile device sensor data, smart home sensor data, smart vehicle sensor data, wearable sensor data, or other sensor data associated with the senior; (iii) analyze the sensor data to determine or identify a need or abnormal condition associated with the senior; (iv) generate an electronic notification of, or detailing, the need or abnormal condition associated with the senior; and/or (v) transmit the electronic notification, via wireless communication or data transmission to a mobile device or other computing device of one or more caregivers and/or service providers, and/or otherwise make the electronic notification accessible via the dedicated website and/or mobile application to facilitate addressing the need and/or abnormal condition associated with the senior.

In another aspect, a multi-sided caregiver platform (MSCP) computer system for matching consumers to providers may be provided. The MSCP computer system may include at least one processor and associated transceiver in communication with at least one memory device. The at least one processor and/or associated transceiver may be programmed to: (i) allow participants to register with the MSCP, such as via wireless communication or data transmission and a dedicated website and/or mobile application, the participants including seniors, caregivers, and/or service providers; (ii) generate or collect sensor data associated with a senior, the sensor data including mobile device sensor data, smart home sensor data, smart vehicle sensor data, wearable sensor data, or other sensor data associated with the senior; (iii) analyze the sensor data to determine or identify a need or abnormal condition associated with the senior; (iv) generate an electronic notification of, or detailing, the need or abnormal condition associated with the senior; and/or (v) transmit the electronic notification, via wireless communication or data transmission to a mobile device or other computing device of one or more caregivers and/or service providers, and/or otherwise make the electronic notification accessible via the dedicated website and/or mobile application to facilitate addressing the need and/or abnormal condition associated with the senior.

The foregoing MSCP computer systems may include additional, less, or alternate functionality, including that discussed elsewhere herein. For instance, to analyze the sensor data to determine or identify a need or abnormal condition associated with the senior, the at least one processor may be configured to: input the sensor data into a machine learning algorithm, model, or program trained to identify needs and/or abnormal conditions from sensor data, including mobile device, smart home, smart vehicle, and/or wearable device sensor data.

A need associated with the senior identified may be a need for transportation services, such as a taxi or transportation company; medical or doctor services; repair services; electrician or plumbing services; pharmaceutical services; grocery delivery services; and/or scheduling an appointment.

An abnormal condition associated with the senior identified may be abnormal, and/or a change in, movement of the senior within a home; movement of the senior outside of a home (i.e., movement about or around town); and/or travel activity of the senior.

An abnormal condition associated with the senior identified may be abnormal, and/or a change in, sleep, or an abnormal, and/or a change in, sleep pattern or routine of the senior. An abnormal condition associated with the senior identified may be abnormal, and/or a change in, eating, or an abnormal, and/or a change in, eating pattern or routine of the senior. An abnormal condition associated with the senior identified may be abnormal, and/or a change in, bathing or showering, or an abnormal, and/or a change in, bathing or showering pattern or routine of the senior.

An abnormal condition associated with the senior identified may be abnormal, and/or a change in, exercise, or an abnormal, and/or a change in, exercise pattern or routine of the senior. An abnormal condition associated with the senior identified may be abnormal, and/or a change in, gait of the senior. An abnormal condition associated with the senior identified may be abnormal, and/or a change in, appearance of the senior.

An abnormal condition associated with the senior identified may be failure to take prescribed medications on time; and/or failure to refill prescribed medications on time.

An abnormal condition associated with the senior identified may be forgetfulness or the onset of forgetfulness; repetitive questions; and/or repetitive speech.

The sensor data may include vehicle telematics data (e.g., braking, cornering, speed, location, acceleration data collected from a smart vehicle or a mobile device), and an abnormal condition associated with the senior identified may be abnormal (or a change in) or risky driving patterns.

The vehicle telematics data or vehicle data may also include vehicle maintenance data, and the need identified may include a need for vehicle maintenance. The MSCP computer system may identify a preferred or recommended car dealership or body shop that is qualified to perform the maintenance, and schedule an appointment to perform the vehicle maintenance, and generate associated electronic messages.

The home sensor data and/or home telematics data may include electricity, energy, fuel, gas, or water usage of the home. The home sensor data and/or home telematics data may also include home maintenance data, and the need identified may include a need for home maintenance. The MSCP computer system may identify a preferred or recommended repairman, electrician, plumber, etc. that is qualified to perform the maintenance, and schedule an appointment to perform the home maintenance, and generate associated electronic messages.

An abnormal condition associated with the senior identified may be an abnormal, and/or a change in, physical condition (e.g., heart rate). An abnormal condition associated with the senior identified may be abnormal, and/or a change in, socialization; social media usage; email or text usage; responsiveness to telephone calls, emails, texts, or other electronic communications; responsive to social media communications; and/or telephone usage.

The MSCP computer system may be further configured to identify and/or schedule a transaction and/or service provider to fulfill the need identified and/or remedy the abnormal condition identified; add the transaction identified to a blockchain associated with the MSCP, senior, and/or one or more caregivers and/or service providers; and/or schedule an appointment with a service provider to fulfill the need identified, and/or remedy the abnormal condition identified.

In another aspect, a computer-implemented method for matching consumers to providers may be provided. The method may be implemented using a multi-sided caregiver platform (MSCP) computer system including at least one processor and associated transceiver in communication with at least one memory device. The method, via the at least one processor and/or associated transceiver, may include (1) allowing participants to register with the MSCP, such as via wireless communication or data transmission and a dedicated website and/or mobile application, the participants including seniors, caregivers, and/or service providers; (2) receiving sensor data associated with a senior via wireless communication or data transmission from a transceiver associated with a mobile device, smart home controller, smart vehicle, or wearable device, the sensor data including mobile device sensor data, smart home sensor data, smart vehicle sensor data, wearable sensor data, or other sensor data associated with the senior; (3) analyzing the sensor data to determine or identify a need or abnormal condition associated with the senior; (4) generating an electronic notification of, or detailing, the need or abnormal condition associated with the senior; and/or (5) transmitting the electronic notification, via wireless communication or data transmission to a mobile device or other computing device of one or more caregivers and/or service providers, and/or otherwise making the electronic notification accessible via the dedicated website and/or mobile application to facilitate addressing the need and/or abnormal condition associated with the senior.

In another aspect, a computer-implemented method for matching consumers to providers may be provided. The method may be implemented using a multi-sided caregiver platform (MSCP) computer system may include at least one processor and associated transceiver in communication with at least one memory device. The method, via the at least one processor and/or associated transceiver, may include: (1) allowing participants to register with the MSCP, such as via wireless communication or data transmission and a dedicated website and/or mobile application, the participants including seniors, caregivers, and/or service providers; (2) generating or collecting sensor data associated with a senior, the sensor data including mobile device sensor data, smart home sensor data, smart vehicle sensor data, wearable sensor data, or other sensor data associated with the senior; (3) analyzing the sensor data to determine or identify a need or abnormal condition associated with the senior; (4) generating an electronic notification of, or detailing, the need or abnormal condition associated with the senior; and/or (5) transmitting the electronic notification, via wireless communication or data transmission to a mobile device or other computing device of one or more caregivers and/or service providers, and/or otherwise making the electronic notification accessible via the dedicated website and/or mobile application to facilitate addressing the need and/or abnormal condition associated with the senior. The foregoing computer-implemented methods may include additional, less, or alternate actions, including those discussed elsewhere herein and with respect to the MSCP computer system.

Machine Learning & Other Matters

The computer systems and computer-implemented methods discussed herein may include additional, less, or alternate actions and/or functionalities, including those discussed elsewhere herein. The computer systems may include or be implemented via computer-executable instructions stored on non-transitory computer-readable media. The methods may be implemented via one or more local or remote processors, transceivers, servers, and/or sensors (such as processors, transceivers, servers, and/or sensors mounted on mobile computing devices, or associated with smart infrastructure or remote servers), and/or via computer executable instructions stored on non-transitory computer-readable media or medium.

In some embodiments, a multi-sided match making computing device is configured to implement machine learning, such that the multi-sided match making computing device "learns" to analyze, organize, and/or process data without being explicitly programmed. Machine learning may be implemented through machine learning methods and algorithms ("ML methods and algorithms"). In an exemplary embodiment, a machine learning module ("ML module") is configured to implement ML methods and algorithms. In some embodiments, ML methods and algorithms are applied to data inputs and generate machine learning outputs ("ML outputs"). Data inputs may include but are not limited to: user data, sensor data, third party data, caregiver data, need data, match data, home telematics data, vehicle telematics data, smart home and smart vehicle data, and/or arrangement data. ML outputs may include but are not limited to: user data, need data, match data, and/or arrangement data. In some embodiments, data inputs may include certain ML outputs.

In some embodiments, at least one of a plurality of ML methods and algorithms may be applied, which may include but are not limited to: linear or logistic regression, instance-based algorithms, regularization algorithms, decision trees, Bayesian networks, cluster analysis, association rule learning, artificial neural networks, deep learning, combined learning, reinforced learning, dimensionality reduction, and support vector machines. In various embodiments, the implemented ML methods and algorithms are directed toward at least one of a plurality of categorizations of machine learning, such as supervised learning, unsupervised learning, and reinforcement learning.

In one embodiment, the ML module employs supervised learning, which involves identifying patterns in existing data to make predictions about subsequently received data. Specifically, the ML module is "trained" using training data, which includes example inputs and associated example outputs. Based upon the training data, the ML module may generate a predictive function which maps outputs to inputs and may utilize the predictive function to generate ML outputs based upon data inputs. The example inputs and example outputs of the training data may include any of the data inputs or ML outputs described above. For example, a ML module may receive training data comprising user data, sensor data, and match data associated with the user data and match data. The ML module may then generate a model which maps match data to aspects of user data and sensor data. The ML module may then generate match data as a ML output based upon subsequently received user data and sensor data.

In another embodiment, an ML module may employ unsupervised learning, which involves finding meaningful relationships in unorganized data. Unlike supervised learning, unsupervised learning does not involve user-initiated training based upon example inputs with associated outputs. Rather, in unsupervised learning, the ML module may organize unlabeled data according to a relationship determined by at least one ML method/algorithm employed by the ML module. Unorganized data may include any combination of data inputs and/or ML outputs as described above. For example, a ML module may receive unlabeled data comprising user data, sensor data, and need data. The ML module may employ an unsupervised learning method such as "clustering" to identify patterns and organize the unlabeled data into meaningful groups. The newly organized data may be used, for example, to generate a model which associates user data and sensor data to determined needs.

In yet another embodiment, a ML module may employ reinforcement learning, which involves optimizing outputs based upon feedback from a reward signal. Specifically, the ML module may receive a user-defined reward signal definition, receive a data input, utilize a decision-making model to generate a ML output based upon the data input, receive a reward signal based upon the reward signal definition and the ML output, and alter the decision-making model so as to receive a stronger reward signal for subsequently generated ML outputs. Other types of machine learning may also be employed, including deep or combined learning techniques.

The reward signal definition may be based upon any of the data inputs or ML outputs described above. For example, a ML module may implement reinforcement learning in generating match data for users. The ML module may utilize a decision-making model to generate match data for users based upon sensor data, and may further receive user-satisfaction data indicating a level of satisfaction experienced by a user and a caregiver who engaged in a transaction. A reward signal may be generated by comparing the user-satisfaction data to the sharing score between the user and the caregiver.

Based upon the reward signal, the ML module may update the decision-making model such that subsequently generated sharing scores more accurately predict user satisfaction. For example, the ML module may determine that a specific driver from a third-party ride sharing service has driven a user to their last four doctor's appointments. The user may have rated the specific driver very highly after each ride. Accordingly, the ML module may learn to automatically book the specific driver for the user when it is determined that the user needs a ride.

Blockchain Functionality

The systems and methods described herein, in some embodiments, relate to, a multi-sided caregiver platform that is managed by using one or more blockchains. In one exemplary embodiment, the process may be performed by a blockchain-based multi-sided caregiver platform computing device. Blockchain functionality may be used to log interactions, transactions, and/or payments between seniors, caregivers, and/or service providers.

A blockchain is a distributed database that maintains a continuously-growing list of ordered records, known as blocks. Each block may contain at least a timestamp and a link to the previous block in the chain. The link to the previous block may be a hash of the previous block. For example, in the case of a smart contract, the first block may contain the initial contract between a senior and a caregiver or service provider. The second block may contain a modification to the smart contract that was requested by the senior and approved by the caregiver or service provider. The second block may contain a hashed copy of the first block as well. The third block may contain one or more additional terms for the smart contract and a hashed copy of the second block. This continues on with each block adding on to the next while containing a hash of the previous blocks in the blockchain.

To ensure the security of the information contained in the blockchain, copies of the blockchain are distributed across multiple computer devices, known as nodes. These nodes maintain the blockchain, update the blockchain when changes occur, and ensure the stability of the blockchain itself. In some embodiments, nodes may also be used to calculate the hash of the previous blocks. As the blockchain grows, the processing power needed to calculate the hash of the previous blocks grows as well. In these embodiments, the processing of the hash may be distributed over multiple computer devices to improve the speed of processing and/or to not overburden the hashing processor. When a node processes (hashes) a block, that node is known as a miner, where the action of validating and hashing the block is also known as mining.

ADDITIONAL CONSIDERATIONS

With the foregoing, users and caregivers may opt-in or register to a multi-sided match making program or other type of program. After the users and caregivers give their affirmative consent or permission, a multi-sided match making remote server may collect data from the mobile devices, user computing devices, smart home controllers, smart vehicles, autonomous or semi-autonomous vehicles, smart infrastructure, smart buildings, smart aerial devices (e.g., drones), and/or other smart devices, such as with the permission or affirmative consent of the users and caregivers. The data collected may be related to user activities and/or user/caregiver schedules and current locations.

As will be appreciated based upon the foregoing specification, the above-described embodiments of the disclosure may be implemented using computer programming or engineering techniques including computer software, firmware, hardware or any combination or subset thereof. Any such resulting program, having computer-readable code means, may be embodied or provided within one or more computer-readable media, thereby making a computer program product, i.e., an article of manufacture, according to the discussed embodiments of the disclosure. The computer-readable media may be, for example, but is not limited to, a fixed (hard) drive, diskette, optical disk, magnetic tape, semiconductor memory such as read-only memory (ROM), and/or any transmitting/receiving medium such as the Internet or other communication network or link. The article of manufacture containing the computer code may be made and/or used by executing the code directly from one medium, by copying the code from one medium to another medium, or by transmitting the code over a network.

These computer programs (also known as programs, software, software applications, "apps", or code) include machine instructions for a programmable processor, and can be implemented in a high-level procedural and/or object-oriented programming language, and/or in assembly/machine language. As used herein, the terms "machine-readable medium" "computer-readable medium" refers to any computer program product, apparatus and/or device (e.g., magnetic discs, optical disks, memory, Programmable Logic Devices (PLDs)) used to provide machine instructions and/or data to a programmable processor, including a machine-readable medium that receives machine instructions as a machine-readable signal. The "machine-readable medium" and "computer-readable medium," however, do not include transitory signals. The term "machine-readable signal" refers to any signal used to provide machine instructions and/or data to a programmable processor.

As used herein, a processor may include any programmable system including systems using micro-controllers, reduced instruction set circuits (RISC), application specific integrated circuits (ASICs), logic circuits, and any other circuit or processor capable of executing the functions described herein. The above examples are example only, and are thus not intended to limit in any way the definition and/or meaning of the term "processor."

As used herein, the terms "software" and "firmware" are interchangeable, and include any computer program stored in memory for execution by a processor, including RAM memory, ROM memory, EPROM memory, EEPROM memory, and non-volatile RAM (NVRAM) memory. The above memory types are example only, and are thus not limiting as to the types of memory usable for storage of a computer program.

In one embodiment, a computer program is provided, and the program is embodied on a computer readable medium. In an exemplary embodiment, the system is executed on a single computer system, without requiring a connection to a server computer. In a further embodiment, the system is being run in a Windows® environment (Windows is a registered trademark of Microsoft Corporation, Redmond, Washington). In yet another embodiment, the system is run on a mainframe environment and a UNIX® server environment (UNIX is a registered trademark of X/Open Company Limited located in Reading, Berkshire, United Kingdom). The application is flexible and designed to run in various different environments without compromising any major functionality. In some embodiments, the system includes multiple components distributed among a plurality of computing devices. One or more components may be in the form of computer-executable instructions embodied in a computer-readable medium. The systems and processes are not limited to the specific embodiments described herein. In addition, components of each system and each process can be practiced independent and separate from other components and processes described herein. Each component and process can also be used in combination with other assembly packages and processes.

In some embodiments, registration of users for the multi-sided match making platform includes opt-in informed consent of users to data usage by the smart home devices, wearable devices, mobile devices, autonomous vehicles, and/or smart vehicles consistent with consumer protection laws and privacy regulations. In some embodiments, the registration data, the user data, and/or other collected data may be anonymized and/or aggregated prior to receipt such that no personally identifiable information (PII) is received. In other embodiments, the system may be configured to receive registration data and/or other collected data that is not yet anonymized and/or aggregated, and thus may be configured to anonymize and aggregate the data. In such embodiments, any PII received by the system is received and processed in an encrypted format, or is received with the consent of the individual with which the PII is associated. In situations in which the systems discussed herein collect personal information about individuals, or may make use of such personal information, the individuals may be provided with an opportunity to control whether such information is collected or to control whether and/or how such information is used. In addition, certain data may be processed in one or more ways before it is stored or used, so that personally identifiable information is removed.

As used herein, an element or step recited in the singular and proceeded with the word "a" or "an" should be understood as not excluding plural elements or steps, unless such exclusion is explicitly recited. Furthermore, references to "exemplary embodiment" or "one embodiment" of the present disclosure are not intended to be interpreted as excluding the existence of additional embodiments that also incorporate the recited features.

The patent claims at the end of this document are not intended to be construed under 35 U.S.C. § 112 (f) unless traditional means-plus-function language is expressly recited, such as "means for" or "step for" language being expressly recited in the claim(s).

This written description uses examples to disclose the disclosure, including the best mode, and also to enable any person skilled in the art to practice the disclosure, including making and using any devices or systems and performing any incorporated methods. The patentable scope of the disclosure is defined by the claims, and may include other examples that occur to those skilled in the art. Such other examples are intended to be within the scope of the claims if they have structural elements that do not differ from the literal language of the claims, or if they include equivalent structural elements with insubstantial differences from the literal language of the claims.

We claim:

1. A multi-sided match making ("MMM") computer system for matching consumers to providers, the MMM computer system comprising at least one processor in communication with at least one memory device and one or more sensors mounted to a vehicle, the at least one processor programmed to:

receive registration data from a user that is associated with the user;

continuously receive user data from the one or more mounted sensors, wherein the user data includes vehicle telematics data associated with the user, wherein the vehicle telematics data includes movement data;

analyze the registration data and the user data to generate a plurality of patterns of behavior of the user including a good driving pattern for the user;

responsive to receiving current vehicle telematics data associated with the user, detect one or more pattern disruptions of the plurality of patterns of behavior of the user, the one or more pattern disruptions including a negative driving pattern for the user;

determine a need based upon the one or more pattern disruptions of the plurality of patterns of behavior of the user;

in response to determining the need of the user, identify one or more caregivers to address the determined need of the user;

receive schedule information from the identified one or more caregivers;

determine availability of the identified one or more caregivers based on the received schedule information of the identified one or more caregivers;

determine that no caregiver associated with the user is available to address the determined need of the user;

determine a third-party service provider that is able to meet the determined need for the user based upon the determined need;

automatically generate arrangements with the determined third-party service provider;

generate a smart contract for the arrangements with the determined third-party service provider;

store the smart contract in a blockchain ledger associated with the user, wherein processing for a hash for the blockchain ledger is distributed over multiple computer devices; and transmit the generated arrangements to a computer device associated with the determined third-party service provider.

2. The MMM computer system of claim 1, wherein the processor is further programmed to:

determine that the need of the user requires transportation of the user to a scheduled event at a defined time and location;

receive, from a computer device associated with the third-party service provider, confirmation from the third-party service provider regarding the arrangements, wherein the confirmation confirms that the third-party service provider will meet the determined need of the user including transporting the user to the location of the scheduled event at the defined time; and send, to a computer device associated with the user, a notification to the user including the confirmed arrangements, wherein the computer device associated with the user is configured to present the notification to the user.

3. The MMM computer system of claim 2, wherein the processor is further programmed to receive feedback from the user regarding the generated arrangements.

4. The MMM computer system of claim 3, wherein the processor is further programmed to store, in the at least one memory device, information including (i) the received user data and registration data, (ii) the determined need of the user, (iii) the matching of the user and the third-party service provider for the determined need of the user, (iv) the generated arrangements, and (v) the feedback from the user regarding the generated arrangements.

5. The MMM computer system of claim 4, wherein the processor is further programmed to determine needs for the user, match the user to the third-party service provider, and generate arrangements for the user by using machine learning techniques on the stored information including the feedback from the user regarding the generated arrangements.

6. The MMM computer system of claim 1, wherein the registration data includes at least one of an age, a birthdate, a height, a weight, a medical history, and preferred doctors and pharmacies of the user, wherein the one or more sensors are associated with at least one of smart home devices and wearable devices, and wherein the need of the user includes at least one of interacting with a smart home device of the user, scheduling an appointment on a mobile device, receiving a notification on the mobile device, conversing on the mobile device, and exercising.

7. A computer-implemented method for matching consumers to providers, the method implemented using a multi-sided match making ("MMM") computer system including at least one processor in communication with at least one memory device and one or more sensors mounted to a vehicle, the method comprising:

receiving registration data from a user that is associated with the user;

continuously receiving user data from the one or more mounted sensors, wherein the user data includes vehicle telematics data associated with the user, wherein the vehicle telematics data includes movement data;

analyzing the registration data and the user data to generate a plurality of patterns of behavior of the user including a good driving pattern for the user;

responsive to receiving current vehicle telematics data associated with the user, detecting one or more pattern disruptions of the plurality of patterns of behavior of the user, the one or more pattern disruptions including a negative driving pattern for the user;

determining a need based upon the one or more pattern disruptions of the plurality of patterns of behavior of the user;

in response to determining the need of the user, identifying one or more caregivers to address the determined need of the user;

receiving schedule information from the identified one or more caregivers;

determining availability of the identified one or more caregivers based on the received schedule information of the identified one or more caregivers;

determining that no caregiver associated with the user is available to address the determined need of the user;

determining a third-party service provider that is able to meet the determined need for the user based upon the determined need;

automatically generating arrangements with the determined third-party service provider;

generating a smart contract for the arrangements with the determined third-party service provider;

storing the smart contract in a blockchain ledger associated with the user, wherein processing for a hash for the blockchain ledger is distributed over multiple computer devices; and transmitting the generated arrangements to a computer device associated with the determined third-party service provider.

8. The computer-implemented method of claim 7, wherein the method further comprises:

determining that the need of the user requires transportation of the user to a scheduled event at a defined time and location;

receiving, from a computer device associated with the third-party service provider, confirmation from the third-party service provider regarding the arrangements, wherein the confirmation confirms that the third-party service provider will meet the determined need of the user including transporting the user to the location of the scheduled event at the defined time; and sending, to a computer device associated with the user, a notification to the user including the confirmed arrangements, wherein the computer device associated with the user is configured to present the notification to the user.

9. The computer-implemented method of claim 7, wherein the method further comprises:

receiving feedback from the user regarding the generated arrangements.

10. The computer-implemented method of claim 7, wherein the method further comprises:

storing, in the at least one memory device, information including (i) the received user data and registration data, (ii) the determined need of the user, (iii) the matching of the user and the third-party service provider for the determined need of the user, (iv) the generated arrangements, and (v) the feedback from the user regarding the generated arrangements.

11. The computer-implemented method of claim 7, wherein the method further comprises:

determining needs for the user, matching the user to the third-party service provider, and generating arrangements for the user by using machine learning techniques on the stored information including the feedback from the user regarding the generated arrangements.

12. The computer-implemented method of claim 7, wherein the registration data includes at least one of an age, a birthdate, a height, a weight, a medical history, and preferred doctors and pharmacies of the user, wherein the one or more sensors are associated with at least one of smart home devices and wearable devices, and wherein the action carried out by the user includes at least one of interacting with a smart home device of the user, scheduling an appointment on a mobile device, receiving a notification on the mobile device, conversing on the mobile device, and exercising.

13. At least one non-transitory computer-readable media having computer-executable instructions thereon, wherein when executed by at least one processor of a multi-sided match making ("MMM") computer system in communication with one or more sensors mounted to a vehicle, cause the at least one processor of the MMM computer system to:

receive registration data from a user that is associated with the user;

continuously receive user data from the one or more mounted sensors, wherein the user data includes vehicle telematics data associated with the user, wherein the vehicle telematics data includes movement data;

analyze the registration data and the user data to generate a plurality of patterns of behavior of the user including a good driving pattern for the user;

responsive to receiving current vehicle telematics data associated with the user, detect one or more pattern disruptions of the plurality of patterns of behavior of the user, the one or more pattern disruptions including a negative driving pattern for the user;

determine a need based upon the one or more pattern disruptions of the plurality of patterns of behavior of the user;

in response to determining the need of the user, identify one or more caregivers to address the determined need of the user;

receive schedule information from the identified one or more caregivers;

determine availability of the identified one or more caregivers based on the received schedule information of the identified one or more caregivers;

determine that no caregiver associated with the user is available to address the determined need of the user;

determine a third-party service provider that is able to meet the determined need for the user based upon the determined need;

automatically generate arrangements with the determined third-party service provider;

generate a smart contract for the arrangements with the determined third-party service provider;

store the smart contract in a blockchain ledger associated with the user, wherein processing for a hash for the blockchain ledger is distributed over multiple computer devices; and transmit the generated arrangements to a computer device associated with the determined third-party service provider.

14. The computer-readable media of claim 13 further causing the at least one processor of the MMM computing device to:

determine that the need of the user requires transportation of the user to a scheduled event at a defined time and location;

receive, from a computer device associated with the third-party service provider, confirmation from the third-party service provider regarding the arrangements, wherein the confirmation confirms that the third-party service provider will meet the determined need of the user including transporting the user to the location of the scheduled event at the defined time; and send, to a computer device associated with the user, a notification to the user including the confirmed arrangements, wherein the computer device associated with the user is configured to present the notification to the user.

15. The computer-readable media of claim 13 further causing the at least one processor of the MMM computing device to:

receive feedback from the user regarding the generated arrangements.

16. The computer-readable media of claim 13 further causing the at least one processor of the MMM computing device to:

store, in the at least one memory device, information including (i) the received user data and registration data, (ii) the determined need of the user, (iii) the matching of the user and the third-party service provider for the determined need of the user, (iv) the generated arrangements, and (v) the feedback from the user regarding the generated arrangements.

17. The computer-readable media of claim 13 further causing the at least one processor of the MMM computing device to:

determine needs for the user, match the user to the third-party service provider, and generate arrangements for the user by using machine learning techniques on the stored information.

18. The MMM computer system of claim 1, wherein the processor is further programmed to:

generate the smart contract between the user and the third-party service provider for the arrangements to meet the determined need; and store the smart contract in a first block of the blockchain ledger associated with the user.

19. The MMM computer system of claim 18, wherein the processor is further programmed to:

determine a second need of the user;

determine an additional third-party service provider to meet the second determined need of the user;

generate a second smart contract between the user and the additional third-party service provider to meet the second determined need; and store the second smart contract in a second block in the blockchain ledger associated with the user, wherein the second block is subsequent to the first block in the blockchain ledger.

* * * * *